(12) United States Patent
Mao et al.

(10) Patent No.: US 10,219,730 B2
(45) Date of Patent: *Mar. 5, 2019

(54) REDOX POLYMERS

(71) Applicant: Abbott Diabetes Care Inc., Alameda, CA (US)

(72) Inventors: Fei Mao, Fremont, CA (US); Adam Heller, Austin, TX (US)

(73) Assignee: Abbott Diabetes Care Inc., Alameda, CA (US)

(*) Notice: Subject to any disclaimer, the term of this patent is extended or adjusted under 35 U.S.C. 154(b) by 261 days.

This patent is subject to a terminal disclaimer.

(21) Appl. No.: 15/134,116

(22) Filed: Apr. 20, 2016

(65) Prior Publication Data

US 2016/0296147 A1    Oct. 13, 2016

Related U.S. Application Data

(63) Continuation of application No. 14/470,660, filed on Aug. 27, 2014, now Pat. No. 9,320,467, which is a
(Continued)

(51) Int. Cl.
*A61B 5/1486* (2006.01)
*C07F 9/00* (2006.01)
(Continued)

(52) U.S. Cl.
CPC .......... *A61B 5/1486* (2013.01); *A61B 5/1477* (2013.01); *A61B 5/14532* (2013.01);
(Continued)

(58) Field of Classification Search
CPC . A61B 5/1473; A61B 5/14532; A61B 5/1486; A61B 5/1477; C07F 9/005;
(Continued)

(56) References Cited

U.S. PATENT DOCUMENTS 5,262,035 A    11/1993  Gregg et al.
5,262,305 A    11/1993  Heller et al.
(Continued)

FOREIGN PATENT DOCUMENTS

CA    2464572       1/2004
EP    1 230 249     8/2002
(Continued)

OTHER PUBLICATIONS

Abruna, H. D. et al., "Rectifying Interfaces Using Two-Layer Films of Electrochemically Polymerized Vinylpyridine and Vinylbipyridine Complexes of Ruthenium and Iron on Electrodes," J. Am. Chem. Soc., vol. 103, No. 1, pp. 1-5 (Jan. 14, 1981).
(Continued)

*Primary Examiner* — Maris R Kessel
(74) *Attorney, Agent, or Firm* — Vorys, Sater, Seymour and Pease LLP

(57) ABSTRACT

Novel transition metal complexes of iron, cobalt, ruthenium, osmium, and vanadium are described. The transition metal complexes can be used as redox mediators in enzyme based electrochemical sensors. In such instances, transition metal complexes accept electrons from, or transfer electrons to, enzymes at a high rate and also exchange electrons rapidly with the sensor. The transition metal complexes include at least one substituted or unsubstituted biimidazole ligand and may further include a second substituted or unsubstituted biimidazole ligand or a substituted or unsubstituted bipyridine or pyridylimidazole ligand. Transition metal complexes attached to polymeric backbones are also described.

20 Claims, 8 Drawing Sheets

Related U.S. Application Data continuation of application No. 13/215,007, filed on Aug. 22, 2011, now Pat. No. 8,828,204, which is a continuation of application No. 12/843,607, filed on Jul. 26, 2010, now Pat. No. 8,168,052, which is a continuation of application No. 11/503,519, filed on Aug. 10, 2006, now Pat. No. 7,918,976, which is a continuation of application No. 10/639,181, filed on Aug. 11, 2003, now Pat. No. 7,090,756, which is a continuation of application No. 09/712,452, filed on Nov. 14, 2000, now Pat. No. 6,605,201.

(60) Provisional application No. 60/165,565, filed on Nov. 15, 1999.

(51) Int. Cl.

| | |
|---|---|
| *C07F 15/00* | (2006.01) |
| *C07F 15/02* | (2006.01) |
| *C07F 15/06* | (2006.01) |
| *C08F 8/44* | (2006.01) |
| *C12Q 1/00* | (2006.01) |
| *A61B 5/145* | (2006.01) |
| *A61B 5/1477* | (2006.01) |
| *C08F 8/42* | (2006.01) |

(52) U.S. Cl.
CPC .......... *C07F 9/005* (2013.01); *C07F 15/0026* (2013.01); *C07F 15/0053* (2013.01); *C07F 15/025* (2013.01); *C07F 15/065* (2013.01); *C08F 8/42* (2013.01); *C08F 8/44* (2013.01); *C12Q 1/004* (2013.01)

(58) Field of Classification Search
CPC ...... C07F 9/0026; C07F 9/002; C07F 9/0053; C07F 9/025; C07F 9/065; G01N 27/327–27/3274; C08F 8/42; C08F 8/44; C12Q 1/004–1/006
See application file for complete search history.

(56) References Cited

U.S. PATENT DOCUMENTS

| | | | |
|---|---|---|---|
| 5,264,092 A | 11/1993 | Skotheim et al. | |
| 5,264,104 A | 11/1993 | Gregg et al. | |
| 5,264,105 A | 11/1993 | Gregg et al. | |
| 5,320,725 A | 6/1994 | Gregg et al. | |
| 5,356,786 A | 10/1994 | Heller et al. | |
| 5,378,628 A | 1/1995 | Grätzel et al. | |
| 5,393,903 A | 2/1995 | Grätzel et al. | |
| 5,410,059 A | 4/1995 | Fraser et al. | |
| 5,437,999 A | 8/1995 | Diebold et al. | |
| 5,463,057 A | 10/1995 | Graetzel | |
| 5,589,326 A | 12/1996 | Deng et al. | |
| 5,593,852 A | 1/1997 | Heller | |
| 5,665,222 A | 9/1997 | Heller | |
| 5,682,884 A * | 11/1997 | Hill ...................... A61B 5/1486 204/403.04 | |
| 5,683,832 A | 11/1997 | Bonhote | |
| 5,789,592 A | 8/1998 | Graetzel et al. | |
| 5,804,049 A | 9/1998 | Chan | |
| 5,846,702 A | 12/1998 | Deng et al. | |
| 5,965,380 A | 10/1999 | Heller | |
| 5,972,199 A | 10/1999 | Heller | |
| 6,083,710 A | 7/2000 | Heller | |
| 6,103,033 A | 8/2000 | Say et al. | |
| 6,120,676 A | 9/2000 | Heller et al. | |
| 6,121,009 A | 9/2000 | Heller | |
| 6,134,461 A | 10/2000 | Say et al. | |
| 6,143,164 A | 11/2000 | Heller et al. | |
| 6,175,752 B1 | 1/2001 | Say et al. | |
| 6,245,988 B1 | 6/2001 | Greatzel et al. | |
| 6,262,264 B1 | 7/2001 | Buck | |
| 6,278,056 B1 | 8/2001 | Sugihara et al. | |
| 6,294,062 B1 | 9/2001 | Buck et al. | |
| 6,338,790 B1 | 1/2002 | Feldman et al. | |
| 6,352,824 B1 | 3/2002 | Buck | |
| 6,605,200 B1 | 8/2003 | Mao | |
| 6,605,201 B1 | 8/2003 | Mao | |
| 6,616,819 B1 | 9/2003 | Liamos et al. | |
| 6,746,582 B2 | 6/2004 | Heller et al. | |
| 7,429,630 B2 | 9/2008 | Liu et al. | |
| 2008/0035479 A1 | 2/2008 | Liu et al. | |

FOREIGN PATENT DOCUMENTS

| | | |
|---|---|---|
| JP | 4-114012 | 4/1992 |
| WO | WO 98/35225 | 8/1998 |
| WO | WO 99/03868 | 1/1999 |
| WO | WO 99/45375 | 9/1999 |
| WO | WO 99/45387 | 9/1999 |
| WO | WO 99/56613 | 11/1999 |
| WO | WO 99/59218 | 11/1999 |
| WO | WO 99/67628 | 12/1999 |
| WO | WO 00/20626 | 4/2000 |
| WO | WO 03/098731 | 11/2003 |

OTHER PUBLICATIONS

Calvert et al., "Synthetic and Mechanistic Investigations of the Reductive Electrochemical Polymerization of Vinyl-Containing Complexes of Iron (II), Ruthenium(II), and Osmium(II)," Inorganic Chemistry, vol. 22, No. 15, 1983, pp. 2151-2162.

Cass, A. et al., "Ferricinum Ion as an Electron Acceptor for Oxido-Reductases," J. Electroanal. Chem., vol. 190, pp. 117-127 (1985).

Cass, A. et al., "Ferrocene-Mediated Enzyme Electrode for Amperometric Determination of Glucose", Anal. Chem., vol. 56, No. 4, pp. 667-671 (Apr. 1984).

Chen, C.Y. et al., "A Biocompatible Needle-Type Glucose Sensor Based on Platinum-Electroplated Carbon Electrode", Applied Biochemistry and Biotechnology, vol. 36, pp. 211-226 (1992).

Chen, C.Y. et al., "Amperometric Needle-Type Glucose Sensor based on a Modified Platinum Electrode with Diminished Response to Interfering Materials", Analytica Chimica Acta, vol. 265, pp. 5-14 (1992).

Csoregi, E. et al., "Design, Characterization, and One-Point in Vivo Calibration of a Subcutaneously Implanted Glucose Electrode," Anal. Chem., vol. 66, No. 19, pp. 31313138 (Oct. 1, 1994).

Csoregi, E. et al., "On-Line Glucose Monitoring by Using Microdialysis Sampling and Amperometric Detection Based on "Wired" Glucose Oxidase in Carbon Paste," Mikrochim. Acta., vol. 121, pp. 31-40 (1995).

Degani, Y. et al., "Direct Electrical Communication between Chemically Modified Enzymes and Metal Electrodes. 2. Methods for Bonding Electron-Transfer Relays to Glucose Oxidase and D-Amino-Acid Oxidase," J. Am. Chem. Soc., vol. 110, No. 8, pp. 2615-2620 (1988).

Degani, Y. et al., "Electrical Communication between Redox Centers of Glucose Oxidase and Electrodes via Electrostatically and Covalently Bound Redox Polymers," J. Am. Chem. Soc., vol. 111, pp. 23572358 (1989).

Degani, Y. et al., Direct Electrical Communication between Chemically Modified Enzymes and Metal Electrodes. 1. Electron Transfer from Glucose Oxidase to Metal Electrodes via Electron Relays, Bound Covalently to the Enzyme, J. Phys. Chem., vol. 91, No. 6, pp. 1285-1289 (1987).

Dicks, J. M., "Ferrocene modified polypyrrole with immobilised glucose oxidase and its application in amperometric glucose microbiosensors," Ann. Biol. clin., vol. 47, pp. 607-619 (1989).

Doherty, A.P. et al., "The Effect of the Nature of the Polymer Backbone on the Stability and the Analytical Response of Polymer-Modified Electrodes", Electroanalysis, vol. 7, No. 4, pp. 333-339 (1995).

Dupray et al. "Synthesis and Characterization of Amide-Derivatized, Polypyridyl-Based Metopolymers" Inorg. Chem. 1996, 35, pp. 6299-6307.

(56) References Cited

OTHER PUBLICATIONS

Fieselmann, B. et al., "Synthesis, Electron Paramagnetic Resonance, and Magnetic Studies on Binuclear Bis(.eta..sup.5-cyclopentadienyl)titanium(III) Compounds with Bridging Pyrazolate, Biimidazolate, and Bibenzimidazolate Anions", Inorganic Chemistry, vol. 17, No. 8, pp. 2078-2084 (1978).
Fischer, H. et al., "Intramolecular Electron Transfer Mediated by 4,4'-Bipyridine and Related Bridging Groups", J. Am. Chem. Soc., vol. 98, No. 18, pp. 5512-5517 (Sep. 1, 1976).
Foulds, N. et al., "Enzyme Entrapment in Electrically Conducting Polymers," J. Chem. Soc., Faraday Trans I., vol. 82, pp. 1259-1264 (1986).
Foulds, N. et al., "Immobilization of Glucose Oxidase in Ferrocene-Modified Pyrrole Polymers," Anal. Chem., vol. 60, No. 22, pp. 2473-2478 (Nov. 15, 1988).
Gholamkhass et al. "Evaluation of Electronic Interaction Matrix Elements for Photoinduced Electron Transfer Processes within Mixed-Valence Complexes" J. Phys. Chem. B 1997, 101, pp. 9010-9021.
Gregg, B. et al., "Cross-Linked Redox Gels Containing Glucose Oxidase for Amperometric Biosensor Applications," Analytical Chemistry, vol. 62, No. 3, pp. 258-263 (Feb. 1, 1990).
Gregg, B. et al., "Redox Polymer Films Containing Enzymes. 1. A Redox-Conducting Epoxy Cement: Synthesis, Characterization, and Electrocatalytic Oxidation of Hydroquinone," J. Phys. Chem., vol. 95, No. 15, pp. 5970-5975 (1991).
Haga, M., "Synthesis and Protonation-deprotonation Reactions of Ruthenium(II) Complexes Containing 2,2'-Bibenzimidazole and Related Ligands", Inorganica Chimica Acta, vol. 75, pp. 29-35 (1983).
Hale, P. et al., "A New Class of Amperometric Biosensor Incorporating a Polymeric Electron-Transfer Mediator," J. Am. Chem. Soc., vol. 111, No. 9, pp. 3482-3484 (1989).
Hedenmo et al. "Reagentless Amperometric Glucose Dehydrogenase Biosensor Based on Electrocatalytic Oxidation of NADH by Osmium Phenanthrolinedione" Analyst 1996, 121, pp. 1891-1895.
Heller, A., "Electrical Connection of Enzyme Redox Centers to Electrodes," J. Phys. Chem., vol. 96, No. 9, pp. 3579-3587 (1992).
Heller, A., "Electrical Wiring of Redox Enzymes," Acc. Chem. Res., vol. 23, No. 5, pp. 129-134 (1990).
Ianniello, R.M. et al. "Immobilized Enzyme Chemically Modified Electrode as an Amperometric Sensor", Anal. Chem., vol. 53, No. 13, pp. 2090-2095 (Nov. 1981).
Ikeda, T. et al., "Glucose oxidase-immobilized benzoquinone-carbon paste electrode as a glucose sensor," Agric. Biol. Chem., vol. 49, No. 2, (1 page—Abstract only) (1985).
Jönsson, G. et al., "An Amperometric Glucose Sensor Made by Modification of a Graphite Electrode Surface with Immobilized Glucose Oxidase and Adsorbed Mediator", Biosensors, vol. 1, pp. 355-368 (1985).
Katakis, I. et al., "Electrostatic Control of the Electron Transfer Enabling Binding of Recombinant Glucose Oxidase and Redox Polyelectrolytes," J. Am. Chem. Soc., vol. 116, No. 8, pp. 3617-3618 (1994).
Katakis, I. et al., "L-.alpha.-Glycerophosphate and L-Lactate Electrodes Based on the Electrochemical "Wiring" of Oxidases," Analytical Chemistry, vol. 64, No. 9, pp. 1008-1013 (May 1, 1992).
Kenausis, G. et al., "'Wiring' of glucose oxidase and lactate oxidase within a hydrogel made with poly(vinly pyridine) complexed with [Os(4,4'-dimethoxy-2,2'-bipyridine).sub.2C1].sup.+/2+," J. Chem. Soc., Faraday Trans., vol. 92, No. 20, pp. 4131-4136 (1996).
Maidan, R. et al., "Elimination of Electrooxidizable Interferant-Produced Currents in Amperometric Biosensors," Analytical Chemistry, vol. 64, No. 23, pp. 2889-2896 (Dec. 1, 1992).
Majumdar et al, "Biimidazole Complexes of $ML_2^{2+}$ [M=Ru or Os, L=2-(phenylazo)-pyridine]. Synthesis Structure and Redox Properties of Mono- and di-nuclear Complexes" J. Chem. Soc. Dalton Trans., 1998, pp. 1569-1574.

Ohara, T. et al., ""Wired" Enzyme Electrodes for Amperometric Determination of Glucose or Lactate in the Presence of Interfering Substances," Analytical Chemistry, vol. 66, No. 15, pp. 2451-2457 (Aug. 1, 1994).
Ohara, T. et al., "Glucose Electrodes Based on Cross-Linked [Os(bpy).sub.2 Cl].sup.+/2+ Complexed Poly(1-vinylimadazole) Films," Analytical Chemistry, vol. 65, No. 23, pp. 3512-3516 (Dec. 1, 1993).
Ohara, T., "Osmium Bipyridyl Redox Polymers Used in Enzyme Electrodes," Platinum Metals Rev., vol. 39, No. 2, pp. 54-62 (Apr. 1995).
Orellana, et al. "Spectroscopic, Electrochemical, and Kinetic Characterization of New Ruthenium(II) Tris-chelates Containing Five-Membered Heterocyclic Moieties" Helvetica Chimica Acta, 1987, vol. 70, No. 8, p. 2073-2086.
Park et al., "Sol-Gel-based Amperometric Glucose Biosensor Incorporating an Osmium Redox Polymer as Mediator," Analytical Communications, 33:271-273 (Aug. 1996).
Pickup, J. et al., "Potentially-implantable, amperometric glucose sensors with mediated electron transfer: improving the operating stability," Biosensors, vol. 4, No. 2, (1 page—Abstract only) (1989).
Pishko, M. et al., "Amperometric Glucose Microelectrodes Prepared Through Immobilization of Glucose Oxidase in Redox Hydrogels", Anal. Chem., vol. 63, No. 20, pp. 2268-2272 (Oct. 15, 1991).
Pollak, A. et al., "Enzyme Immobilization by Condensation Copolymerization into Cross-Linked Polyacrylamide Gels,"J. Am. Chem. Soc., vol. 102, No. 20, pp. 6324-6336 (1980).
Reeder, K. et al., "Solution-State Spin-Equilibrium Properties of the Tris[2-(2-pyridyl)imidazole]iron(II) and Tris[2-(2-pyridyl)benzimidazole]iron(II) Cations", Inorganic Chemistry, vol. 17, No. 4, pp. 1071-1075 (1978).
Sasso, S. et al., "Electropolymerized 1,2-Diaminobenzene as a Means to Prevent Interferences and Fouling and to Stabilize Immobilized Enzyme in Electrochemical Biosensors", Anal. Chem., vol. 62, No. 11, pp. 1111-1117 (Jun. 1, 1990).
Schalkhammer, et al., "Electrochemical Glucose Sensors on Permselective Non-conducting Substituted Pyrrole Polymers", Sensors and Actuators, vol. B4, pp. 273-281 (1991).
Schmehl et al., "The Effect of Redox Site Concentration on the Rate of Mediated Oxidation of Solution Substrates by a Redox Copolymer Film," J. Electroanal. Chem. 152, 1983, pp. 97-109.
Sugiyarto, et al. "Structural, Magnetic and Mössbauer Studies of Bis(2,6-bis(pyrazol-3-yl)pyridine)iron(II) Triflate and its Hydrates" Australian Journal of Chemistry, 1987, vol. 40, No. 5, p. 775-783.
Surridge et al., Electron and Counterion Diffusion Constants in Mixed-Valent Polymeric Osmium Bipyridine Films, The Journal of Physical Chemistry, vol. 98, No. 3, 1994, pp. 917-923.
Surridge et al., Site Dilution of Osmium Polypyridine Complexes in Three Electron-Hopping Conductive Polymer Films on Electrodes by Electrochemical Copolymerization of Osmium with Ruthenium and with Zinc Complexes, Inorganic Chemistry, vol. 29, No. 24, 1990, pp. 4950-4955.
Taylor, C. et al., "'Wiring' of glucose oxidase within a hydrogel made with polyvinyl imidazole complexed with [(Os-4,4'-dimethoxy-2,2'-bipyridine)C1].sup.+/2+," Journal of Electroanalytical Chemistry, vol. 396, pp. 511-515 ( )1995).
Trojanowicz, M. et al., "Enzyme Entrapped Polypyrrole Modified Electrode for Flow-Injection Determination of Glucose," Biosensors & Bioelectronics, vol. 5, pp. 149-156 (1990).
Ye, L. et al., "High Current Density "Wired" Quinoprotein Glucose Dehydrogenase Electrode," Anal. Chem., vol. 65, No. 3, pp. 238-241 (Feb. 1, 1993).
Yildiz, A., "Evaluation of an Improved Thin-Layer Electrode", Analytical Chemistry vol. 40, No. 7, pp. 1018-1024 (Jun. 1968).
Yu et al, "Synthesis, Metal Complex Formation, and Electronic Properties of a Novel Conjugate Polymer with a Tridentate 2,6-Bis(benzimidazol-2-yl)pyridine Ligand" Macromolecules, 1999, 32, pp. 5251-5256.

\* cited by examiner

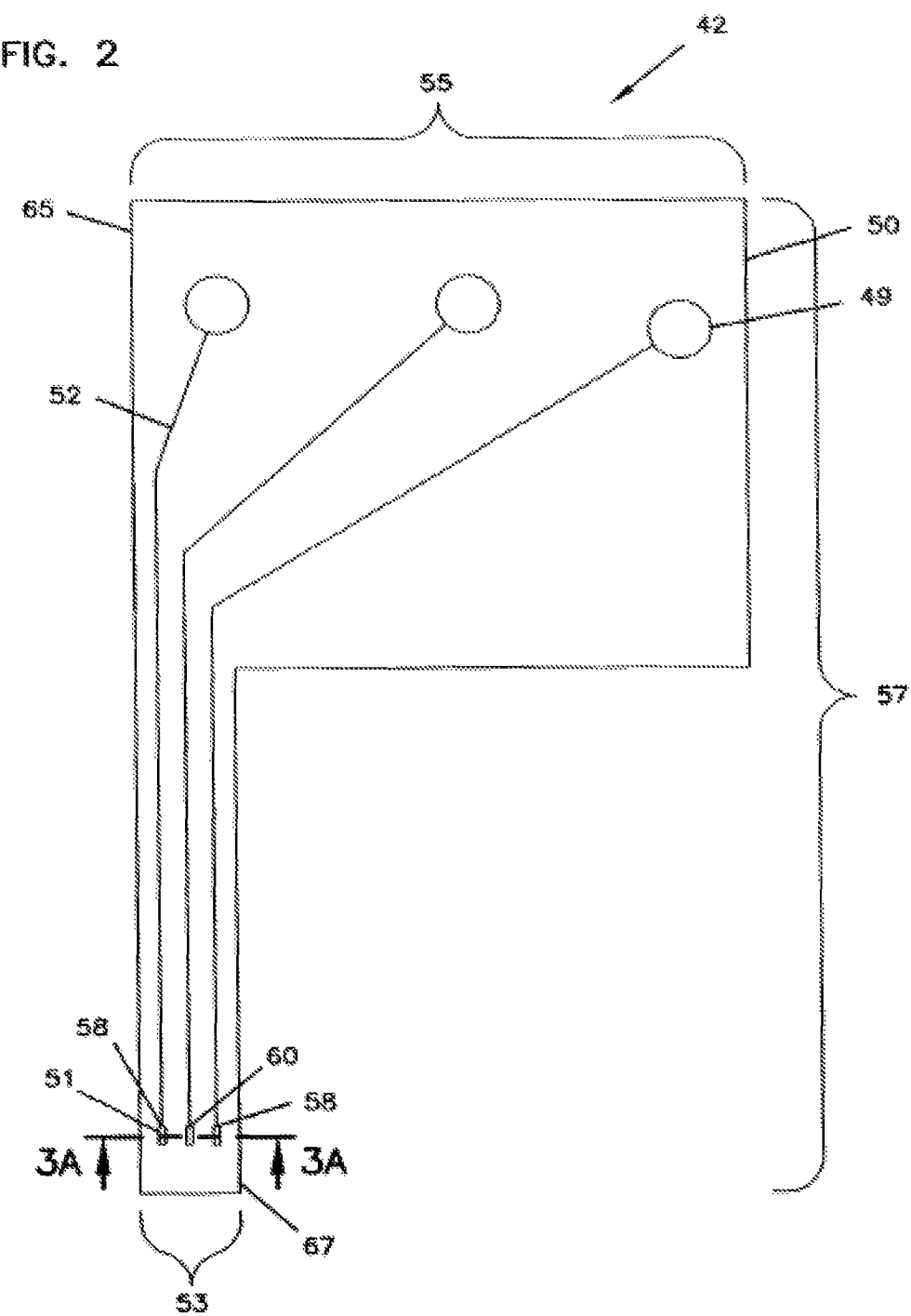

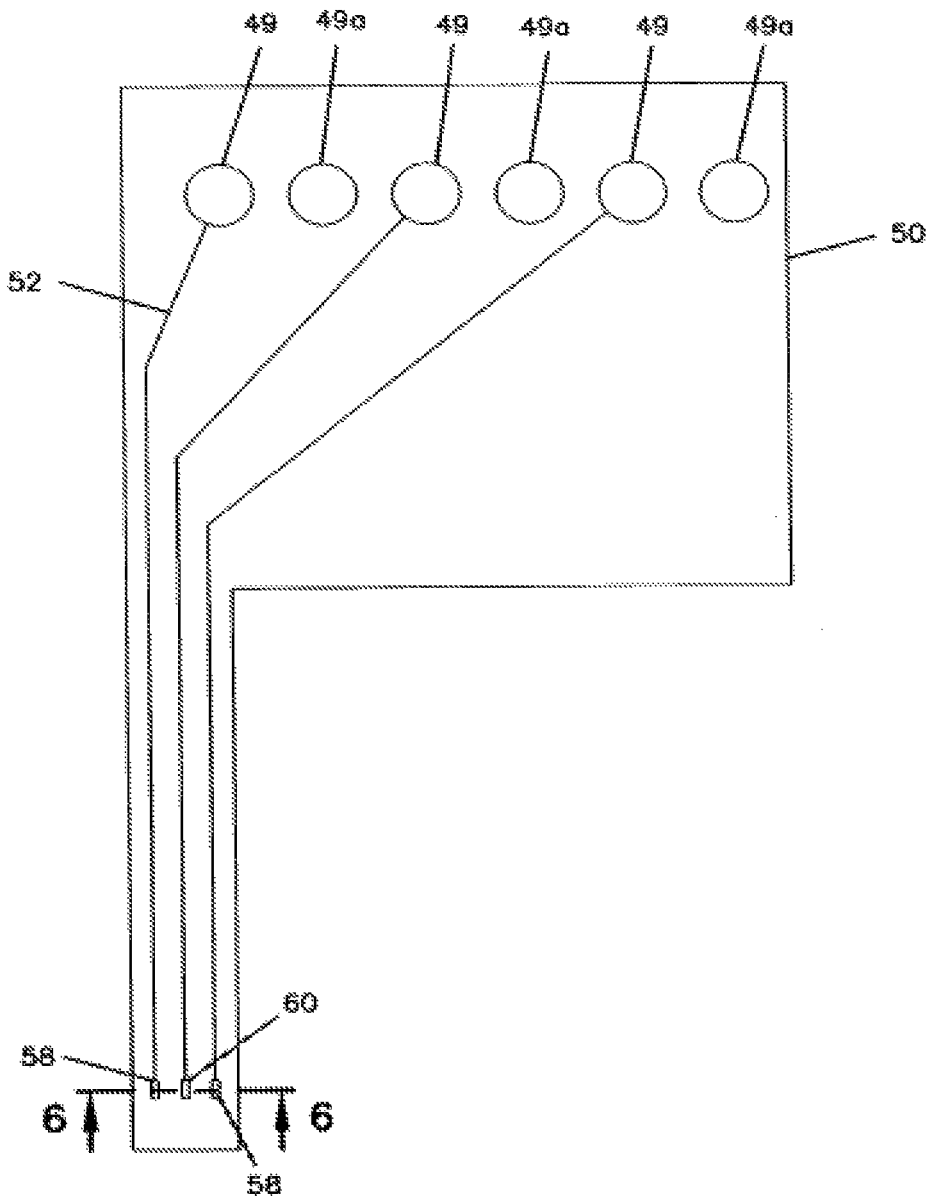

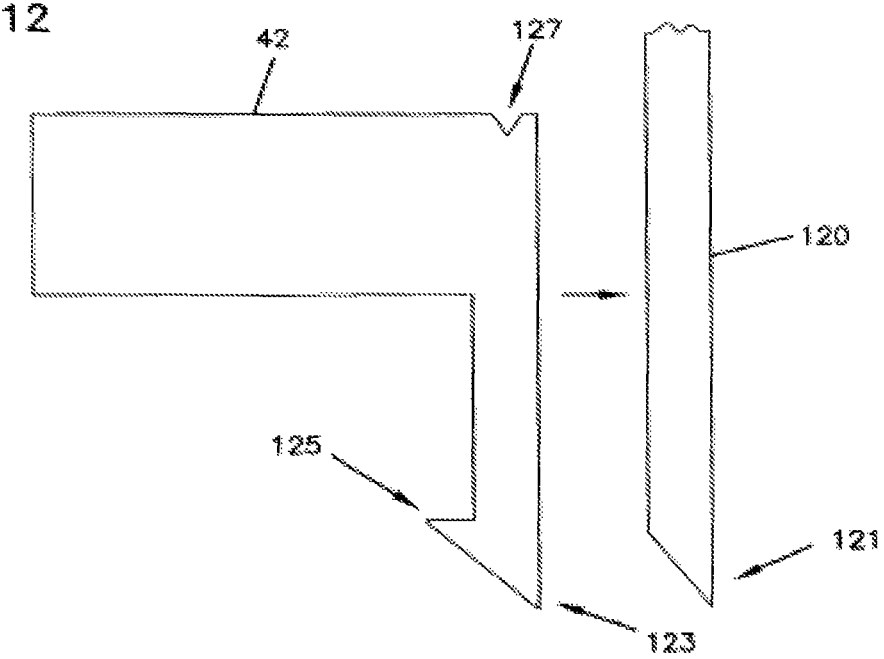

REDOX POLYMERS

RELATED APPLICATIONS

This application is a continuation of U.S. patent application Ser. No. 14/470,660, filed on Aug. 27, 2014, issued as U.S. Pat. No. 9,320,467, which is a continuation of U.S. patent application Ser. No. 13/215,007, filed on Aug. 22, 2011, issued as U.S. Pat. No. 8,828,204, which is a continuation of U.S. patent application Ser. No. 12/843,607, filed on Jul. 26, 2010, issued as U.S. Pat. No. 8,168,052, which is a continuation of U.S. patent application Ser. No. 11/503,519, filed on Aug. 10, 2006, issued as U.S. Pat. No. 7,918,976, which is a continuation of U.S. patent application Ser. No. 10/639,181, filed Aug. 11, 2003, issued as U.S. Pat. No. 7,090,756, which is a continuation of U.S. patent application Ser. No. 09/712,452, filed Nov. 14, 2000, issued as U.S. Pat. No. 6,605,201, which claims benefit of U.S. Provisional Patent Application Ser. No. 60/165,565, filed Nov. 15, 1999, which are incorporated herein by reference.

FIELD OF THE INVENTION

This invention relates to transition metal complexes with at least one bidentate ligand containing at least one imidazole ring. In addition, the invention relates to the preparation of the transition metal complexes and to the use of the transition metal complexes as redox mediators.

BACKGROUND OF THE INVENTION

Enzyme based electrochemical sensors are widely used in the detection of analytes in clinical, environmental, agricultural and biotechnological applications. Analytes that can be measured in clinical assays of fluids of the human body include, for example, glucose, lactate, cholesterol, bilirubin and amino acids. Levels of these analytes in biological fluids, such as blood, are important for the diagnosis and the monitoring of diseases.

Electrochemical assays are typically performed in cells with two or three electrodes, including at least one measuring or working electrode and one reference electrode. In three electrode systems, the third electrode is a counter-electrode. In two electrode systems, the reference electrode also serves as the counter-electrode. The electrodes are connected through a circuit, such as a potentiostat. The measuring or working electrode is a non-corroding carbon or metal conductor. Upon passage of a current through the working electrode, a redox enzyme is electrooxidized or electroreduced. The enzyme is specific to the analyte to be detected, or to a product of the analyte. The turnover rate of the enzyme is typically related (preferably, but not necessarily, linearly) to the concentration of the analyte itself, or to its product, in the test solution.

The electrooxidation or electroreduction of the enzyme is often facilitated by the presence of a redox mediator in the solution or on the electrode. The redox mediator assists in the electrical communication between the working electrode and the enzyme. The redox mediator can be dissolved in the fluid to be analyzed, which is in electrolytic contact with the electrodes, or can be applied within a coating on the working electrode in electrolytic contact with the analyzed solution. The coating is preferably not soluble in water, though it may swell in water. Useful devices can be made, for example, by coating an electrode with a film that includes a redox mediator and an enzyme where the enzyme is catalytically specific to the desired analyte, or its product. In contrast to a coated redox mediator, a diffusional redox mediator, which can be soluble or insoluble in water, functions by shuttling electrons between, for example, the enzyme and the electrode. In any case, when the substrate of the enzyme is electrooxidized, the redox mediator transports electrons from the substrate-reduced enzyme to the electrode; when the substrate is electroreduced, the redox mediator transports electrons from the electrode to the substrate-oxidized enzyme.

Recent enzyme based electrochemical sensors have employed a number of different redox mediators such as monomeric ferrocenes, quinoid-compounds including quinines (e.g., benzoquinones), nickel cyclamates, and ruthenium ammines. For the most part, these redox mediators have one or more of the following limitations: the solubility of the redox mediators in the test solutions is low, their chemical, light, thermal, or pH stability is poor, or they do not exchange electrons rapidly enough with the enzyme or the electrode or both. Additionally, the redox potentials of many of these reported redox mediators are so oxidizing that at the potential where the reduced mediator is electrooxidized on the electrode, solution components other than the analyte are also electrooxidized; in other cases they are so reducing that solution components, such as, for example, dissolved oxygen are also rapidly electroreduced. As a result, the sensor utilizing the mediator is not sufficiently specific.

SUMMARY OF THE INVENTION

The present invention is directed to novel transition metal complexes. The present invention is also directed to the use of the complexes as redox mediators. The preferred redox mediators typically exchange electrons rapidly with enzymes and electrodes, are stable, and have a redox potential that is tailored for the electrooxidation of analytes, exemplified by glucose.

One embodiment of the invention is a transition metal complex having the formula:

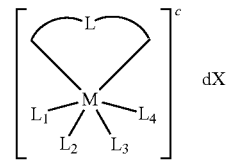

M is cobalt, ruthenium, osmium, or vanadium. L is selected from the group consisting of:

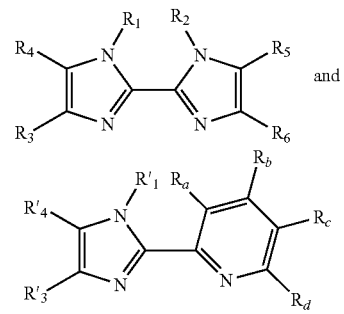

and $R_1$, $R_2$, and $R'_1$ are independently substituted or unsubstituted alkyl, alkenyl, or aryl groups. $R_3$, $R_4$, $R_5$, $R_6$, $R'_3$, $R'_4$, $R_a$, $R_b$, $R_c$, and $R_d$ are independently —H, —F, —Cl, —Br, —I, —$NO_2$, —CN, —$CO_2H$, —$SO_3H$, —$NHNH_2$, —SH, aryl, alkoxycarbonyl, alkylaminocarbonyl, dialkylaminocarbonyl, —OH, alkoxy, —$NH_2$, alkylamino, dialkylamino, alkanoylamino, arylcarboxamido, hydrazino, alkylhydrazino, hydroxylamino, alkoxyamino, alkylthio, alkenyl, aryl, or alkyl. c is an integer selected from −1 to −5 or +1 to +5 indicating a positive or negative charge. X represents at least one counter ion and d is an integer from 1 to 5 representing the number of counter ions, X. $L_1$, $L_2$, $L_3$ and $L_4$ are other ligands.

Another embodiment is a redox mediator having the formula:

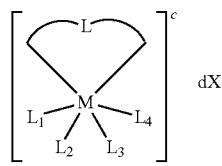

M is iron, cobalt, ruthenium, osmium, or vanadium. L is a bidentate ligand comprising at least one imidazole ring. c is an integer selected from −1 to −5 or +1 to +5 indicating a positive or negative charge. X represents at least one counter ion and d is an integer from 1 to 5 representing the number of counter ions, X. $L_1$, $L_2$, $L_3$ and $L_4$ are other ligands.

Another embodiment is a sensor that includes the redox polymer, a working electrode, and a counter electrode. The redox polymer is disposed proximate to the working electrode.

Yet another embodiment is a polymer that includes a polymeric backbone and a transition metal complex having the following formula:

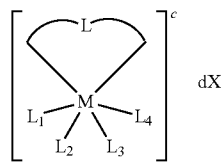

M is iron, cobalt, ruthenium, osmium, or vanadium. L is a bidentate ligand comprising at least one imidazole ring. c is an integer selected from −1 to −5 or +1 to +5 indicating a positive or negative charge. X represents at least one counter ion and d is an integer from 1 to 5 representing the number of counter ions, X. $L_1$, $L_2$, $L_3$ and $L_4$ are other ligands where at least one of L, $L_1$, $L_2$, $L_3$ and $L_4$ couples to the polymeric backbone.

The redox polymers are generally capable of carrying electrons between an enzyme and an electrode. The polymers can be useful in electrochemical biosensors. One embodiment is a polymeric transition metal complex that includes a polymeric backbone, a plurality of spacers, and a plurality of transition metal complexes. Each of the spacers is covalently coupled to and extending from the polymeric backbone and includes at least one non-cyclic functional group selected from the group consisting of —($CR^rR^s$)—, —O—, —S—, —C(O)O—, —$S(O)_2NR^k$—, —OC(O)$NR^m$—, —OC(S)$NR^n$—, —C(O)$NR^t$—, —$NR^u$—, —$CR^v$=N—O—, —$CR^w$=$NNR^x$—, and —($SiR^yR^z$)—, where $R^r$ and $R^s$ are independently hydrogen, chlorine, fluorine, or substituted or unsubstituted alkyl, alkoxy, alkenyl, or alkynyl and $R^k$, $R^m$, $R^n$, $R^t$, $R^u$, $R^v$, $R^w$, $R^x$, $R^y$, and $R^z$ are independently hydrogen or substituted or unsubstituted alkyl. Each of the transition metal complexes has the formula:

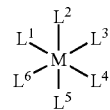

M is osmium, ruthenium, vanadium, cobalt, or iron. $L^1$ is a ligand that includes a heterocycle and is coordinatively bound to M via a heteroatom of the heterocycle. $L^2$, $L^3$, $L^4$, $L^5$, and $L^6$ are ligands, where each of $L^1$, $L^2$, $L^3$, $L^4$, $L^5$, and $L^6$ is independently a monodentate ligand or combined with at least one other ligand to form a multidentate ligand. At least one of $L^1$, $L^2$, $L^3$, $L^4$, $L^5$, and $L^6$ is covalently coupled to one of the spacers.

Another embodiment is a polymeric transition metal complex that includes a reaction product of
a) a polymer having a polymeric backbone and a plurality of pendant groups extending from the polymeric backbone, where at least a portion of the pendant groups have a reactive group and
b) a plurality of transition metal complexes, each transition metal complex having the formula:

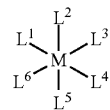

M is osmium, ruthenium, vanadium, cobalt, or iron. $L^1$ is a ligand comprising a heterocycle and coordinatively bound to M via a heteroatom of the heterocycle. $L^2$, $L^3$, $L^4$, $L^5$, and $L^6$ are ligands, where each of $L^1$, $L^2$, $L^3$, $L^4$, $L^5$, and $L^6$ is independently a monodentate ligand or combined with at least one other ligand to form a multidentate ligand. At least one of $L^1$, $L^2$, $L^3$, $L^4$, $L^5$, and $L^6$ includes a reactive group that is capable of reacting with one of the reactive groups of the polymer.

Yet another embodiment is a polymeric transition metal complex that includes a polymeric backbone, a plurality of spacers, and a plurality of transition metal complexes. Each spacer is covalently coupled to and extends from the polymeric backbone and includes a flexible chain of at least four atoms. Each transition metal complex has the formula:

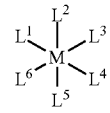

M is osmium, ruthenium, vanadium, cobalt, or iron. $L^1$ is a ligand comprising a heterocycle and coordinatively bound to M via a heteroatom of the heterocycle. $L^2$, $L^3$, $L^4$, $L^5$, and $L^6$ are ligands, where each of $L^1$, $L^2$, $L^3$, $L^4$, $L^5$, and $L^6$ is independently a monodentate ligand or combined to form one or more multidentate ligands. At least one of $L^1$, $L^2$, $L^3$, $L^4$, $L^5$, and $L^6$ is covalently coupled to one of the spacers.

Another embodiment of the invention is a redox mediator that includes any of the polymeric transition metal complexes described above.

Yet another embodiment is a sensor that includes the redox mediator, a working electrode, and a counter electrode. The redox mediator is disposed proximate to the working electrode. Preferably, the redox mediator is disposed on the working electrode. More preferably, the redox mediator is non-leachably disposed on the working electrode.

BRIEF DESCRIPTION OF THE DRAWINGS

The invention may be more completely understood in consideration of the following detailed description of various embodiments of the invention in connection with the accompanying drawings, in which:

FIG. 2 is a top view of one embodiment of an analyte sensor, according to the invention;

FIG. 10 is a top view of the analyte sensor of FIG. 6;

FIG. 12 is an expanded side view of one embodiment of a sensor and an insertion device, according to the invention.

DETAILED DESCRIPTION

Figure 1:
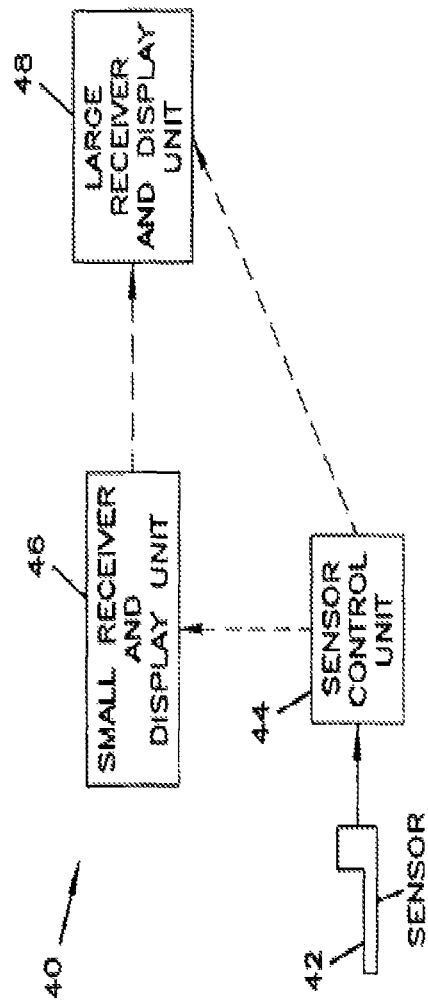
FIG. 1 is a block diagram of one embodiment of a subcutaneous analyte monitor using a subcutaneously implantable analyte sensor, according to the invention.

When used herein, the following definitions define the stated term:

The term "alkyl" includes linear or branched, saturated aliphatic hydrocarbons. Examples of alkyl groups include methyl, ethyl, n-propyl, isopropyl, n-butyl, tert-butyl and the like. Unless otherwise noted, the term "alkyl" includes both alkyl and cycloalkyl groups.

The term "alkoxy" describes an alkyl group joined to the remainder of the structure by an oxygen atom. Examples of alkoxy groups include methoxy, ethoxy, n-propoxy, isopropoxy, butoxy, tert-butoxy, and the like. In addition, unless otherwise noted, the term 'alkoxy' includes both alkoxy and cycloalkoxy groups.

The term "alkenyl" describes an unsaturated, linear or branched aliphatic hydrocarbon having at least one carbon-carbon double bond. Examples of alkenyl groups include ethenyl, 1-propenyl, 2-propenyl, 1-butenyl, 2-methyl-1-propenyl, and the like.

A "reactive group" is a functional group of a molecule that is capable of reacting with another compound to couple at least a portion of that other compound to the molecule. Reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron-withdrawing groups such as sulfo, nitro, cyano, or halo groups; or carboxylic acids activated by carbodiimides.

A "substituted" functional group (e.g., substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, —OH, —$NH_2$, alkylamino, dialkylamino, trialkylammonium, alkanoylamino, arylcarboxamido, hydrazino, alkylthio, alkenyl, and reactive groups.

A "biological fluid" is any body fluid or body fluid derivative in which the analyte can be measured, for example, blood, interstitial fluid, plasma, dermal fluid, sweat, and tears.

An "electrochemical sensor" is a device configured to detect the presence of or measure the concentration or amount of an analyte in a sample via electrochemical oxidation or reduction reactions. These reactions typically can be transduced to an electrical signal that can be correlated to an amount or concentration of analyte.

A "redox mediator" is an electron transfer agent for carrying electrons between an analyte or an analyte-reduced or analyte-oxidized enzyme and an electrode, either directly, or via one or more additional electron transfer agents.

"Electrolysis" is the electrooxidation or electroreduction of a compound either directly at an electrode or via one or more electron transfer agents (e.g., redox mediators or enzymes).

The term "reference electrode" includes both a) reference electrodes and b) reference electrodes that also function as counter electrodes (i.e., counter/reference electrodes), unless otherwise indicated.

The term "counter electrode" includes both a) counter electrodes and b) counter electrodes that also function as reference electrodes (i.e., counter/reference electrodes), unless otherwise indicated.

The term "flexible chain" refers to a saturated C4 to C24 chain where, optionally, one or more of the carbon atoms are replaced by heteroatoms (such as, for example, oxygen, sulfur, or nitrogen) as part of, for example, an ether, thioether, or amine group. The chain can be substituted or unsubstituted.

Generally, the present invention relates to transition metal complexes of iron, cobalt, ruthenium, osmium, and vanadium having at least one bidentate ligand containing an imidazole ring. The invention also relates to the preparation of the transition metal complexes and to the use of the transition metal complexes as redox mediators. In at least some instances, the transition metal complexes have one or more of the following characteristics: redox potentials in a particular range, the ability to exchange electrons rapidly with electrodes, the ability to rapidly transfer electrons to or rapidly accept electrons from an enzyme to accelerate the kinetics of electrooxidation or electroreduction of an analyte in the presence of an enzyme or another analyte-specific redox catalyst. For example, a redox mediator may accelerate the electrooxidation of glucose in the presence of glucose oxidase or PQQ-glucose dehydrogenase, a process that can be useful for the selective assay of glucose in the presence of other electrochemically oxidizable species. Compounds having the formula 1 are examples of transition metal complexes of the present invention.

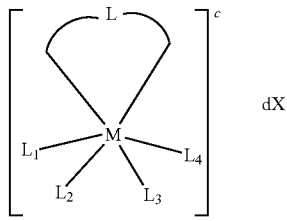

1

M is a transition metal and is typically iron, cobalt, ruthenium, osmium, or vanadium. Ruthenium and osmium are particularly suitable for redox mediators.

L is a bidentate ligand containing at least one imidazole ring. One example of L is a 2,2'-biimidazole having the following structure 2:

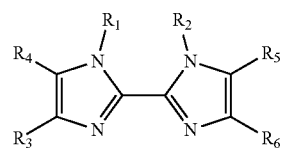

2

$R_1$ and $R_2$ are substituents attached to two of the 2,2'-biimidazole nitrogens and are independently substituted or unsubstituted alkyl, alkenyl, or aryl groups. Generally, $R_1$ and $R_2$ are unsubstituted C1 to C12 alkyls. Typically, $R_1$ and $R_2$ are unsubstituted C1 to C4 alkyls. In some embodiments, both $R_1$ and $R_2$ are methyl.

$R_3$, $R_4$, $R_5$, and $R_6$ are substituents attached to carbon atoms of the 2,2'-biimidazole and are independently —H, —F, —Cl, —Br, —I, —$NO_2$, —CN, —$CO_2H$, —$SO_3H$, alkoxycarbonyl, alkylaminocarbonyl, dialkylaminocarbonyl, —OH, alkoxy, —$NH_2$, alkylamino, dialkylamino, alkanoylamino, arylcarboxamido, hydrazino, alkylhydrazino, hydroxylamino, alkoxyamino, alkylthio, alkenyl, aryl, or alkyl. Alternatively, $R_3$ and $R_4$ in combination or $R_5$ and $R_6$ in combination independently form a saturated or unsaturated 5- or 6-membered ring. An example of this is a 2,2'-bibenzoimidazole derivative. Typically, the alkyl and alkoxy portions are C1 to C12. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. Generally, $R_3$, $R_4$, $R_5$, and $R_6$ are independently —H or unsubstituted alkyl groups. Typically, $R_3$, $R_4$, $R_5$, and $R_6$ are —H or unsubstituted C1 to C12 alkyls. In some embodiments, $R_3$, $R_4$, $R_5$, and $R_6$ are all —H.

Another example of L is a 2-(2-pyridyl)imidazole having the following structure 3:

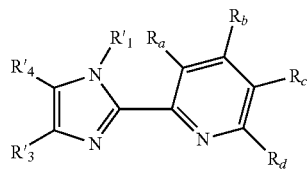

3

$R'_1$ is a substituted or unsubstituted aryl, alkenyl, or alkyl. Generally, $R'_1$ is a substituted or unsubstituted C1-C12 alkyl. $R'_1$ is typically methyl or a C1-C12 alkyl that is optionally substituted with a reactive group.

$R'_3$, $R'_4$, $R_a$, $R_b$, $R_c$, and $R_d$ are independently —H, —F, —Cl, —Br, —I, —$NO_2$, —CN, —$CO_2H$, —$SO_3H$, —$NHNH_2$, —SH, alkoxylcarbonyl, alkylaminocarbonyl, dialkylaminocarbonyl, —OH, alkoxy, —$NH_2$, alkylamino, dialkylamino, alkanoylamino, arylcarboxamido, hydrazino, alkylhydrazino, hydroxylamino, alkoxylamino, alkylthio, alkenyl, aryl, or alkyl. Alternatively, $R_c$ and $R_d$ in combination or $R'_3$ and $R'_4$ in combination can form a saturated or unsaturated 5- or 6-membered ring. Typically, the alkyl and alkoxy portions are C1 to C12. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. Generally, $R'_3$, $R'_4$, $R_a$, $R_b$, $R_c$ and $R_d$ are independently —H or unsubstituted alkyl groups. Typically, $R_a$ and $R_c$ are —H and $R'_3$, $R'_4$, $R_b$, and $R_d$ are —H or methyl.

c is an integer indicating the charge of the complex. Generally, c is an integer selected from −1 to −5 or +1 to +5 indicating a positive or negative charge. For a number of osmium complexes, c is +2 or +3.

X represents counter ion(s). Examples of suitable counter ions include anions, such as halide (e.g., fluoride, chloride, bromide or iodide), sulfate, phosphate, hexafluorophosphate, and tetrafluoroborate, and cations (preferably, monovalent cations), such as lithium, sodium, potassium, tetralkylammonium, and ammonium. Preferably, X is a halide, such as chloride. The counter ions represented by X are not necessarily all the same.

d represents the number of counter ions and is typically from 1 to 5.

$L_1$, $L_2$, $L_3$ and $L_4$ are ligands attached to the transition metal via a coordinative bond. $L_1$, $L_2$, $L_3$ and $L_4$ can be monodentate ligands or, in any combination, bi-, ter-, or tetradentate ligands For example, $L_1$, $L_2$, $L_3$ and $L_4$ can combine to form two bidentate ligands such as, for example, two ligands selected from the group of substituted and unsubstituted 2,2'-biimidazoles, 2-(2-pyridyl)imidizoles, and 2,2'-bipyridines Examples of other $L_1$, $L_2$, $L_3$ and $L_4$ combinations of the transition metal complex include:
  (A) $L_1$ is a monodentate ligand and $L_2$, $L_3$ and $L_4$ in combination form a terdentate ligand;
  (B) $L_1$ and $L_2$ in combination are a bidentate ligand, and $L_3$ and $L_4$ are the same or different monodentate ligands;
  (C) $L_1$ and $L_2$ in combination, and $L_3$ and $L_4$ in combination form two independent bidentate ligands which can be the same or different; and
  (D) $L_1$, $L_2$, $L_3$ and $L_4$ in combination form a tetradentate ligand.

Examples of suitable monodentate ligands include, but are not limited to, —F, —Cl, —Br, —I, —CN, —SCN, —OH, H₂O, NH₃, alkylamine, dialkylamine, trialkylamine, alkoxy or heterocyclic compounds. The alkyl or aryl portions of any of the ligands are optionally substituted by —F, —Cl, —Br, —I, alkylamino, dialkylamino, trialkylammonium (except on aryl portions), alkoxy, alkylthio, aryl, or a reactive group. Any alkyl portions of the monodentate ligands generally contain 1 to 12 carbons. More typically, the alkyl portions contain 1 to 6 carbons. In other embodiments, the monodentate ligands are heterocyclic compounds containing at least one nitrogen, oxygen, or sulfur atom. Examples of suitable heterocyclic monodentate ligands include imidazole, pyrazole, oxazole, thiazole, pyridine, pyrazine and derivatives thereof. Suitable heterocyclic monodentate ligands include substituted and unsubstituted imidazole and substituted and unsubstituted pyridine having the following general formulas 4 and 5, respectively:

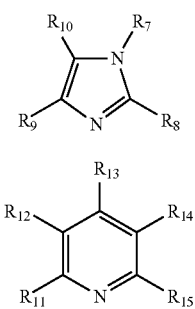

With regard to formula 4, $R_7$ is generally a substituted or unsubstituted alkyl, alkenyl, or aryl group. Typically, $R_7$ is a substituted or unsubstituted C1 to C12 alkyl or alkenyl. The substitution of inner coordination sphere chloride anions by imidazoles does not typically cause a large shift in the redox potential in the oxidizing direction, differing in this respect from substitution by pyridines, which typically results in a large shift in the redox potential in the oxidizing direction. $R_8$, $R_9$ and $R_{10}$ are independently —H, —F, —Cl, —Br, —I, —NO₂, —CN, —CO₂H, —SO₃H, —NHNH₂, —SH, aryl, alkoxycarbonyl, alkylaminocarbonyl, dialkylaminocarbonyl, —OH, alkoxy, —NH₂, alkylamino, dialkylamino, alkanoylamino, arylcarboxamido, hydrazino, alkylhydrazino, hydroxylamino, alkoxyamino, alkylthio, alkenyl, aryl, or alkyl. Alternatively, $R_9$ and $R_{10}$, in combination, form a fused 5 or 6-membered ring that is saturated or unsaturated. The alkyl portions of the substituents generally contain 1 to 12 carbons and typically contain 1 to 6 carbon atoms. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. In some embodiments, $R_8$, $R_9$ and $R_{10}$ are —H or substituted or unsubstituted alkyl. Preferably, $R_8$, $R_9$ and $R_{10}$ are —H.

With regard to Formula 5, $R_{11}$, $R_{12}$, $R_{13}$, $R_{14}$ and $R_{15}$ are independently —H, —F, —Cl, —Br, —I, —NO₂, —CN, —CO₂H, alkoxycarbonyl, alkylaminocarbonyl, dialkylaminocarbonyl, —OH, alkoxy, —NH₂, alkylamino, dialkylamino, alkanoylamino, arylcarboxamido, hydrazino, alkylhydrazino, hydroxylamino, alkoxyamino, alkylthio, alkenyl, aryl, or alkyl. The alkyl or aryl portions of any of the substituents are optionally substituted by —F, —Cl, —Br, —I, alkylamino, dialkylamino, trialkylammonium (except for aryl portions), alkoxy, alkylthio, aryl, or a reactive group. Generally, $R_{11}$, $R_{12}$, $R_{13}$, $R_{14}$ and $R_{15}$ are —H, methyl, C1-C2 alkoxy, C1-C2 alkylamino, C2-C4 dialkylamino, or a C1-C6 lower alkyl substituted with a reactive group.

One example includes $R_{11}$ and $R_{15}$ as —H, $R_{12}$ and $R_{14}$ as the same and —H or methyl, and $R_{13}$ as —H, C1 to C12 alkoxy, —NH₂, C1 to C12 alkylamino, C2 to C24 dialkylamino, hydrazino, C1 to C12 alkylhydrazino, hydroxylamino, C1 to C12 alkoxyamino, C1 to C12 alkylthio, or C1 to C12 alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

Examples of suitable bidentate ligands include, but are not limited to, amino acids, oxalic acid, acetylacetone, diaminoalkanes, ortho-diaminoarenes, 2,2'-biimidazole, 2,2'-bioxazole, 2,2'-bithiazole, 2-(2-pyridyl)imidazole, and 2,2'-bipyridine and derivatives thereof. Particularly suitable bidentate ligands for redox mediators include substituted and unsubstituted 2,2'-biimidazole, 2-(2-pyridyl)imidazole and 2,2'-bipyridine. The substituted 2,2' biimidazole and 2-(2-pyridyl)imidazole ligands can have the same substitution patterns described above for the other 2,2'-biimidazole and 2-(2-pyridyl)imidazole ligand. A 2,2'-bipyridine ligand has the following general formula 6:

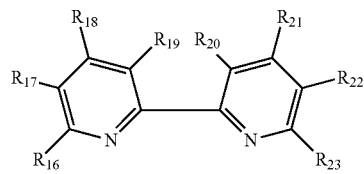

$R_{16}$, $R_{17}$, $R_{18}$, $R_{19}$, $R_{20}$, $R_{21}$, $R_{22}$ and $R_{23}$ are independently —H, —F, —Cl, —Br, —I, —NO₂, —CN, —CO₂H, —SO₃H, —NHNH₂, —SH, aryl, alkoxycarbonyl, alkylaminocarbonyl, dialkylaminocarbonyl, —OH, alkoxy, —NH₂, alkylamino, dialkylamino, alkanoylamino, arylcarboxamido, hydrazino, alkylhydrazino, hydroxylamino, alkoxyamino, alkylthio, alkenyl, or alkyl. Typically, the alkyl and alkoxy portions are C1 to C12. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

Specific examples of suitable combinations of $R_{16}$, $R_{17}$, $R_{18}$, $R_{19}$, $R_{20}$, $R_{21}$, $R_{22}$ and $R_{23}$ include $R_{16}$ and $R_{23}$ as H or methyl; $R_{17}$ and $R_{22}$ as the same and —H or methyl; and $R_{19}$ and $R_{20}$ as the same and —H or methyl. An alternative combination is where one or more adjacent pairs of substituents $R_{16}$ and $R_{17}$, on the one hand, and $R_{22}$ and $R_{23}$, on the other hand, independently form a saturated or unsaturated 5- or 6-membered ring. Another combination includes $R_{19}$ and $R_{20}$ forming a saturated or unsaturated five or six membered ring.

Another combination includes $R_{16}$, $R_{17}$, $R_{19}$, $R_{20}$, $R_{22}$ and $R_{23}$ as the same and —H and $R_{18}$ and $R_{21}$ as independently —H, alkoxy, —NH₂, alkylamino, dialkylamino, alkylthio, alkenyl, or alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. As an example, $R_{18}$ and $R_{21}$ can be the same or different and are —H, C1-C6 alkyl, C1-C6 amino, C1 to C12 alkylamino, C2 to C12 dialkylamino, C1 to C12 alkylthio, or C1 to C12 alkoxy, the alkyl portions of any of the substituents are optionally substituted by a —F, —Cl, —Br, —I, aryl, C2 to C12 dialkylamino, C3 to C18 trialkylammonium, C1 to C6 alkoxy, C1 to C6 alkylthio or a reactive group.

Examples of suitable terdentate ligands include, but are not limited to, diethylenetriamine, 2,2',2"-terpyridine, 2,6-bis(N-pyrazolyl)pyridine, and derivatives of these compounds. 2,2',2"-terpyridine and 2,6-bis(N-pyrazolyl)pyridine have the following general formulas 7 and 8 respectively:

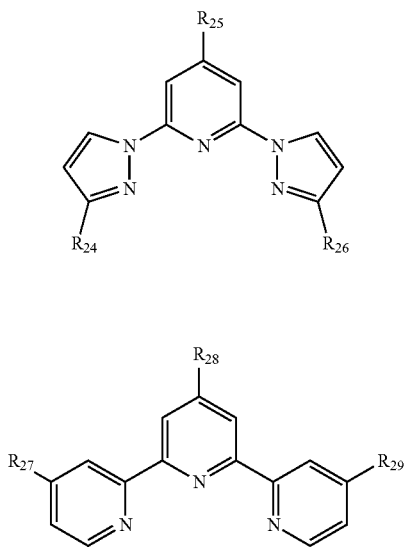

With regard to formula 7, $R_{24}$, $R_{25}$ and $R_{26}$ are independently —H or substituted or unsubstituted C1 to C12 alkyl. Typically, $R_{24}$, $R_{25}$ and $R_{26}$ are —H or methyl and, in some embodiments, $R_{24}$ and $R_{26}$ are the same and are —H. Other substituents at these or other positions of the compounds of formulas 7 and 8 can be added.

With regard to formula 8, $R_{27}$, $R_{28}$ and $R_{29}$ are independently —H, —F, —Cl, —Br, —I, —NO$_2$, —CN, —CO$_2$H, —SO$_3$H, —NHNH$_2$, —SH, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxylamino, alkylthio, alkenyl, aryl, or alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. Typically, the alkyl and alkoxy groups are C1 to C12 and, in some embodiments, $R_{27}$ and $R_{29}$ are the same and are —H.

Examples of suitable tetradentate ligands include, but are not limited to, triethylenetriamine, ethylenediaminediacetic acid, tetraaza macrocycles and similar compounds as well as derivatives thereof.

Examples of suitable transition metal complexes are illustrated using Formula 9 and 10:

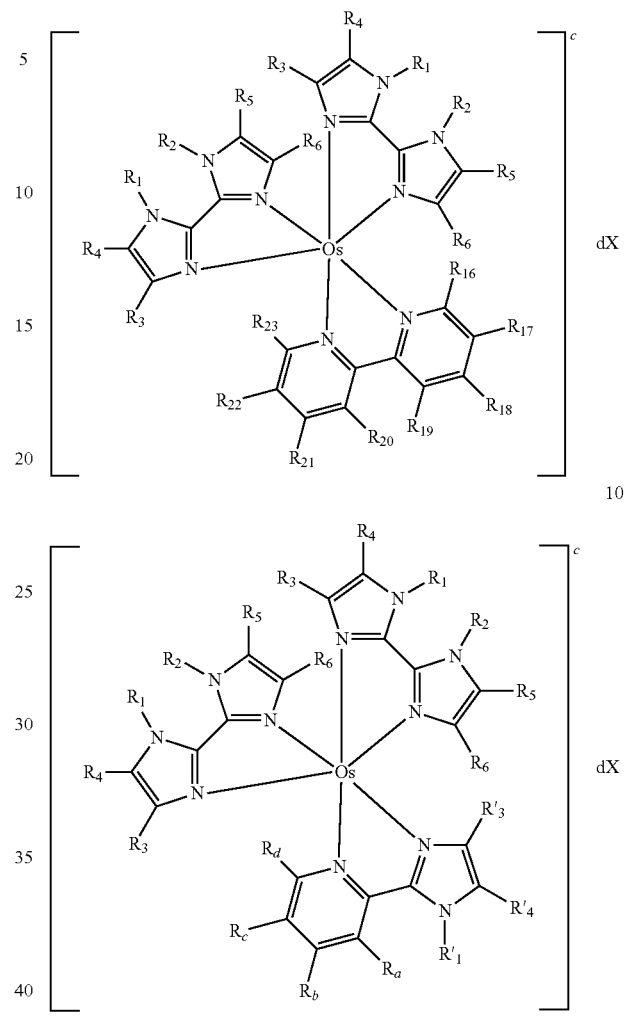

With regard to transition metal complexes of formula 9, the metal osmium is complexed to two substituted 2,2'-biimidazole ligands and one substituted or unsubstituted 2,2'-bipyridine ligand. $R_1$, $R_2$, $R_3$, $R_4$, $R_5$, $R_6$, $R_{16}$, $R_{17}$, $R_{18}$, $R_{19}$, $R_{20}$, $R_{21}$, $R_{22}$, $R_{23}$, c, d, and X are the same as described above.

In one embodiment, $R_1$ and $R_2$ are methyl; $R_3$, $R_4$, $R_5$, $R_6$, $R_{16}$, $R_{17}$, $R_{19}$, $R_{20}$, $R_{22}$ and $R_{23}$ are —H; and $R_{18}$ and $R_{21}$ are the same and are —H, methyl, or methoxy. Preferably, $R_{18}$ and $R_{21}$ are methyl or methoxy.

In another embodiment, $R_1$ and $R_2$ are methyl; $R_3$, $R_4$, $R_5$, $R_6$, $R_{16}$, $R_{17}$, $R_{18}$, $R_{19}$, $R_{20}$, $R_{22}$ and $R_{23}$ are —H; and $R_{21}$ is halo, C1 to C12 alkoxy, C1 to C12 alkylamino, or C2 to C24 dialkylamino. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. For example, $R_{21}$ is a C1 to C12 alkylamino or C2 to C24 dialkylamino, the alkyl portion(s) of which are substituted with a reactive group, such as a carboxylic acid, activated ester, or amine. Typically, the alkylamino group has 1 to 6 carbon atoms and the dialkylamino group has 2 to 8 carbon atoms.

With regard to transition metal complexes of formula 10, the metal osmium is complexed to two substituted 2,2'- biimidazole ligands and one substituted or unsubstituted 2-(2-pyridyl)imidazole ligand. $R_1$, $R_2$, $R_3$, $R_4$, $R_5$, $R_6$, $R'_1$, $R'_3$, $R'_4$, $R_a$, $R_b$, $R_c$, $R_d$, c, d, and X are the same as described above.

In one embodiment, $R_1$ and $R_2$ are methyl; $R_3$, $R_4$, $R_5$, $R_6$, $R'_3$, $R'_4$ and $R_d$ are independently —H or methyl; $R_a$ and $R_c$ are the same and are —H; and $R_b$ is C1 to C12 alkoxy, C1 to C12 alkylamino, or C2 to C24 dialkylamino. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

Typically, each of the transition metal complexes has the formula:

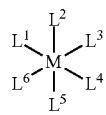

M is a transition metal and is typically osmium, ruthenium, vanadium, cobalt, or iron. $L^1$, $L^2$, $L^3$, $L^4$, $L^5$, and $L^6$ are ligands and are independently monodentate ligands or two or more of the ligands can be combined to form one or more multidentate ligands. $L^1$, in particular, is a ligand that includes a heterocycle and is coordinatively bound to M via a heteroatom of the heterocycle. At least one of $L^1$, $L^2$, $L^3$, $L^4$, $L^5$, and $L^6$ is covalently coupled to one of the spacers.

Any combination of monodentate and multidentate ligands can be used. For example, $L^2$, $L^3$, $L^4$, $L^5$, and $L^6$ can combine to form three bidentate ligands such as, for example, three bidentate ligands selected from substituted and unsubstituted 2,2'-biimidazoles, 2-(2-pyridyl)imidazoles, and 2,2'-bipyridines. Examples of other combinations of $L^2$, $L^3$, $L^4$, $L^5$, and $L^6$ include:

(A) Two monodentate ligands and two bidentate ligands;
(B) Four monodentate ligands and one bidentate ligand;
(C) Three monodentate ligands and one tridentate ligand;
(D) One monodentate ligand, one bidentate ligand, and one tridentate ligand;
(E) Two monodentate ligands and one tetradentate ligand; and
(F) One bidentate ligand and one tetradentate ligand.

A list of specific examples of preferred transition metal complexes with respective redox potentials is shown in Table 1.

TABLE 1

Redox Potentials of Selected Transition Metal Complexes

| Complex | Structure | $E_{1/2}$(vs Ag/AgCl)/mV* |
|---|---|---|
| I | [Os(1,1'-dimethyl-2,2'-biimidazole)$_2$(4-dimethylamino-2,2'-bipyridine)]Cl$_3$ | −110 |
| II | [Os(1,1'-dimethyl-2,2'-biimidazole)$_2$(4-methylamino-2,2'-bipyridine)]Cl$_3$ | −100 |

TABLE 1-continued
Redox Potentials of Selected Transition Metal Complexes
| Complex | Structure | $E_{1/2}$(vs Ag/AgCl)/mV* |
|---|---|---|
| III | 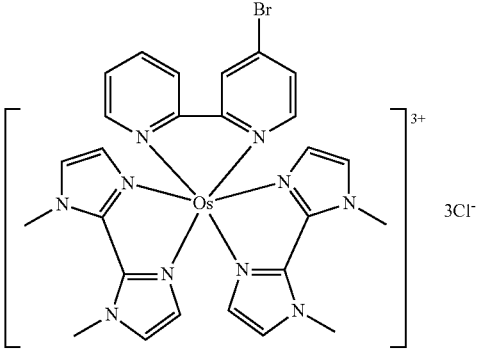 [Os(1,1'-dimethyl-2,2'-biimidazole)$_2$(4-bromo-2,2'-bipyridine)]Cl$_3$ | 128 |
| IV | 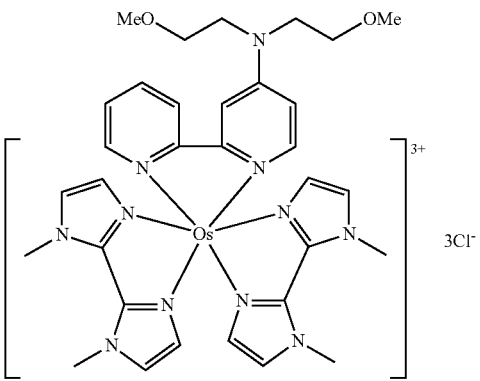 [Os(1,1'-dimethyl-2,2'-biimidazole)$_2$(4-di(2-methoxyethyl)amino-2,2'-bipyridine)]Cl$_3$ | −86 |
| V | 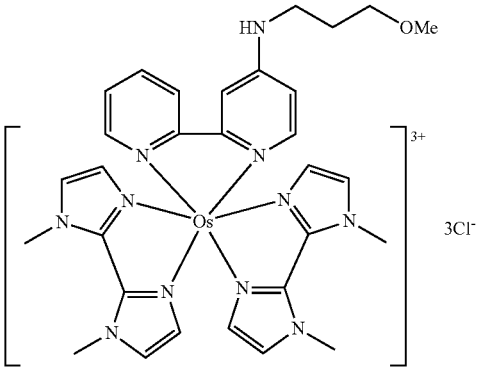 [Os(1,1'-dimethyl-2,2'-biimidazole)$_2$(4-(3-methoxypropyl)amino-2,2'-bipyridine)]Cl$_3$ | −97 |

TABLE 1-continued
Redox Potentials of Selected Transition Metal Complexes
| Complex | Structure | $E_{1/2}$(vs Ag/AgCl)/mV* |
|---|---|---|
| VI | 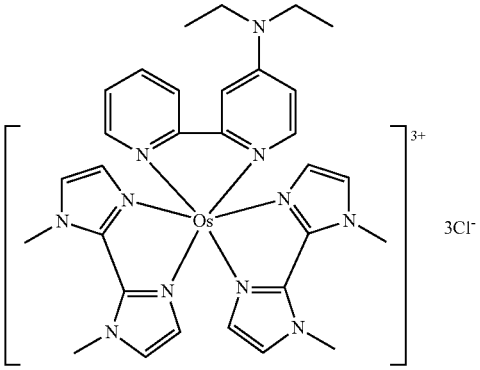<br>[Os(1,1'-dimethyl-2,2'-biimidazole)$_2$(4-diethylamino-2,2'-bipyridine)]Cl$_3$ | −120 |
| VII | 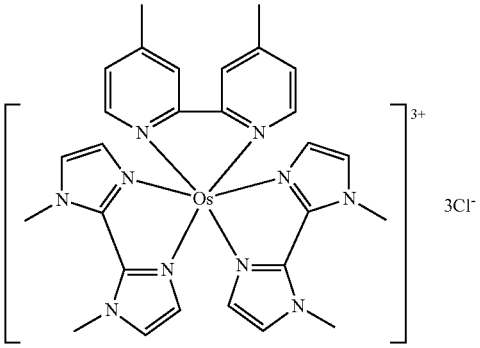<br>[Os(1,1'-dimethyl-2,2'-biimidazole)$_2$(4,4'-dimethyl-2,2'-bipyridine)]Cl$_3$ | 32 |
| VIII | 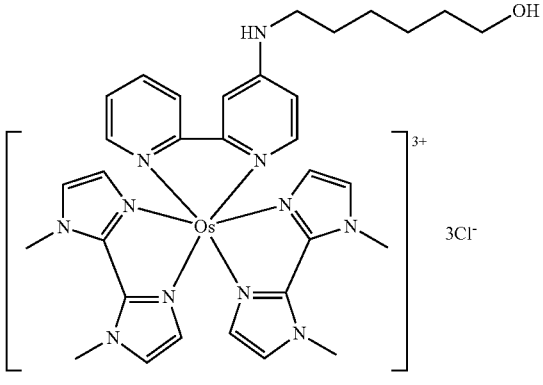<br>[Os(1,1'-dimethyl-2,2'-biimidazole)$_2$(4-(6-hydroxyhexyl)amino-2,2'-bipyridine)]Cl$_3$ | −100 |

TABLE 1-continued
Redox Potentials of Selected Transition Metal Complexes
| Complex | Structure | $E_{1/2}$(vs Ag/AgCl)/mV* |
|---|---|---|
| IX | 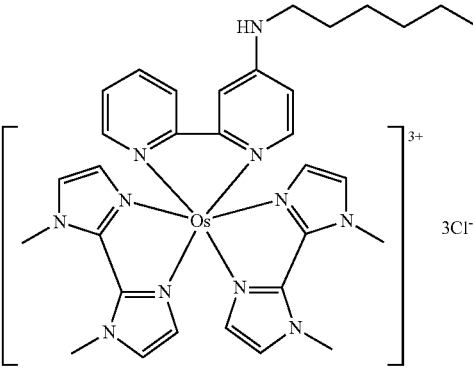 [Os(1,1'-dimethyl-2,2'-biimidazole)$_2$(4-(6-aminohexyl)amino-2,2'-bipyridine)]Cl$_3$ | −93 |
| X | 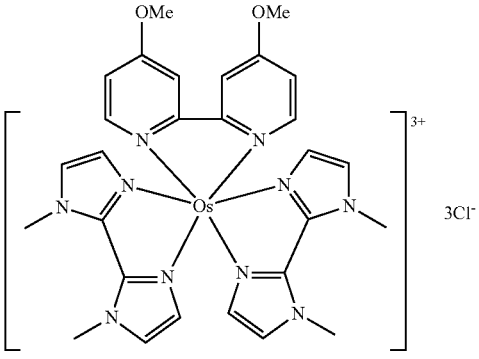 [Os(1,1'-dimethyl-2,2'-biimidazole)$_2$(4-methoxypyridine)$_2$]Cl$_3$ | −125 |
| XI | 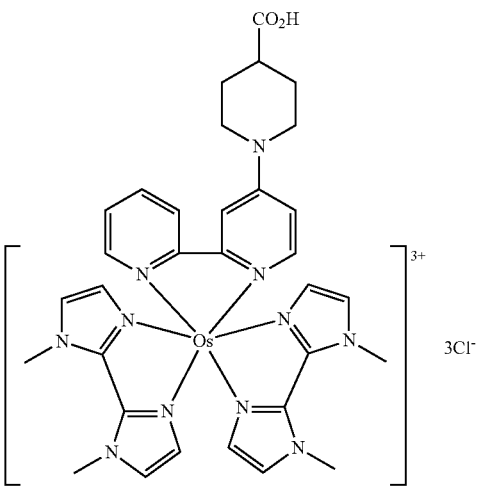 [Os(1,1'-dimethyl-2,2'-biimidazole)$_2$(4-(N-(4-carboxy)piperidino)-2,2'-bipyridine)]Cl$_3$ | −60 |

TABLE 1-continued
Redox Potentials of Selected Transition Metal Complexes
| Complex | Structure | $E_{1/2}$(vs Ag/AgCl)/mV* |
|---|---|---|
| XII | 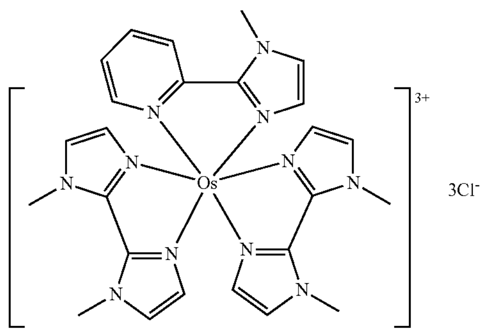 | −74 |
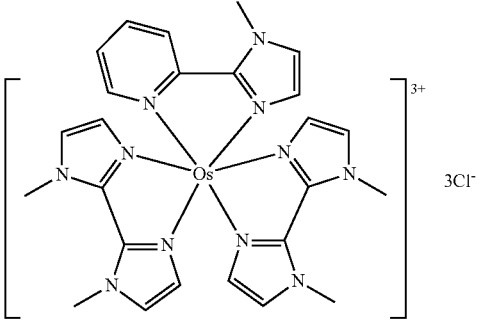
[Os(1,1'-dimethyl-2,2'-biimidazole)$_2$(1-methyl-2-(2-pyridyl)imidazole)]Cl$_3$
| XIII | | −97 |
|---|---|---|
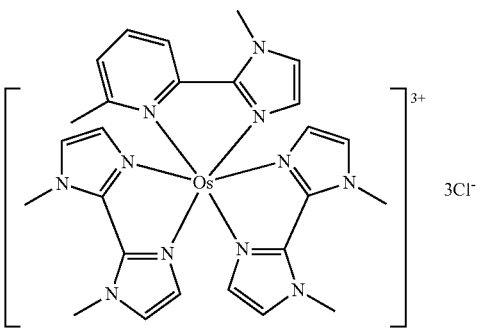
[Os(1,1'-dimethyl-2,2'-biimidazole)$_2$(1-methyl-2-(6-methylpyrid-2-yl)imidazole)]Cl$_3$
| IVX | | −81 |
|---|---|---|
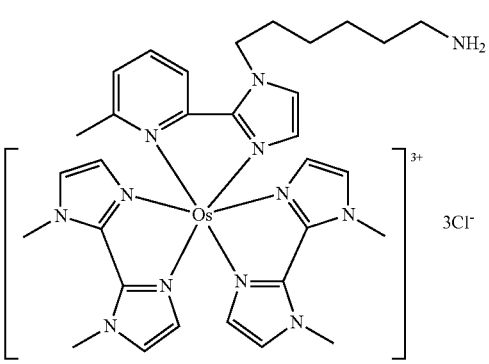
[Os(1,1'-dimethyl-2,2'-biimidazole)$_2$(1-(6-aminohexyl)-2-(6-methylpyrid-2-yl)imidazole)]Cl$_3$ TABLE 1-continued Redox Potentials of Selected Transition Metal Complexes

| Complex | Structure | $E_{1/2}$(vs Ag/AgCl)/mV* |
|---|---|---|
| VX | 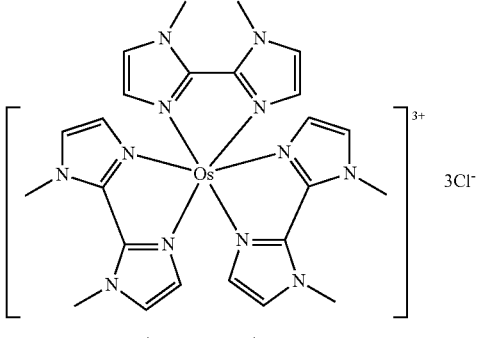 [Os(3,3'-dimethyl-2,2'-biimidazole)$_3$]Cl$_3$ | −230 |

*Redox potentials were estimated by averaging the positions of the reduction wave peaks and the oxidation wave peaks of cyclic voltammograms (CVs) obtained in pH 7 PBS buffer with a glassy carbon working electrode, a graphite counter electrode and a standard Ag/AgCl reference electrode at a sweep rate of 50 mV/s.

The transition metal complexes of Formula 1 also include transition metal complexes that are coupled to a polymeric backbone through one or more of L, $L_1$, $L_2$, $L_3$, and $L_4$. Additional examples of suitable transition metal complexes are described in U.S. patent application Ser. No. 09/712,065, entitled "Polymeric Transition Metal Complexes and Uses Thereof", filed on even date herewith, incorporated herein by reference. In some embodiments, the polymeric backbone has functional groups that act as ligands of the transitional metal complex. Such polymeric backbones include, for example, poly(4-vinylpyridine) and poly(N-vinylimidazole) in which the pyridine and imidazole groups, respectively, can act as monodentate ligands of the transition metal complex. In other embodiments, the transition metal complex can be the reaction product between a reactive group on a precursor polymer and a reactive group on a ligand of a precursor transition metal complex (such as a complex of Formula 1 where one of L, $L_1$, $L_2$, $L_3$ and $L_4$ includes a reactive group as described above). Suitable precursor polymers include, for example, poly(acrylic acid) (Formula 11), styrene/maleic anhydride copolymer (Formula 12), methylvinylether/maleic anhydride copolymer (GANTREX polymer) (Formula 13), poly(vinylbenzylchloride) (Formula 14), poly(allylamine) (Formula 15), polylysine (Formula 16), carboxy-poly(vinylpyridine (Formula 17), and poly(sodium 4-styrene sulfonate) (Formula 18).

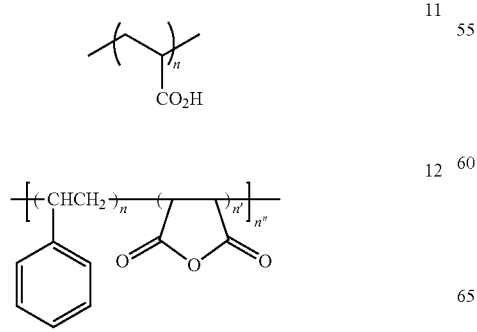

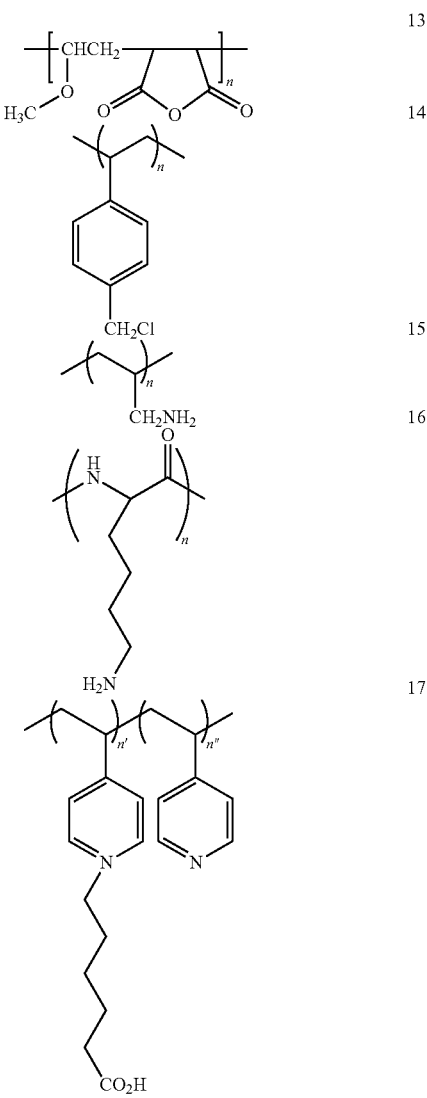

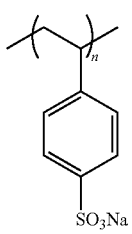

18

The spacer couples the transition metal complex to the polymeric backbone. In some embodiments, the spacer includes at least one non-cyclic functional group selected from the group consisting of —(CR'R$^s$)—, —O—, —S—, —C(O)O—, —S(O)$_2$NR$^k$—, —OC(O)NR$^m$—, —OC(S)NR$^n$, —C(O)NR$^t$—, —NR$^u$—, —CR$^v$=N—O—, —CR$^w$=NNR$^x$—, and —(SiR$^y$R$^z$)—, where R$^r$ and R$^s$ are independently hydrogen, chlorine, fluorine, or substituted or unsubstituted alkyl, alkoxy, alkenyl, or alkynyl and R$^k$, R$^m$, R$^n$, R$^t$, R$^u$, R$^v$, R$^w$, R$^x$, R$^y$, and R$^z$ are independently hydrogen or substituted or unsubstituted alkyl. Preferably, the spacer includes at least four, and, more preferably, at least eight of these non-cyclic functional groups. Preferably, the non-cyclic functional group(s) is/are selected fiom the group consisting of —(CR'R$^s$)—, —O—, —S—, —C(O)O—, —S(O)$_2$NR$^k$—, —OC(O)NR$^m$—, —OC(S)NR$^n$, —C(O)NR$^t$—, —NR$^u$—, —CR$^v$=N—O—, —CR$^w$=NNR$^x$—, and —(SiR$^y$R$^z$)—, where R$^k$, R$^m$, R$^n$, R$^t$, R$^u$, R$^v$, R$^w$, R$^x$, R$^y$, and R$^z$ are independently selected from the group consisting of hydrogen and substituted or unsubstituted alkyl. In one embodiment, the preferred spacer includes a 4 to 30 atom long linear segment, the linear segment having any combination of the following bonds to form the 4 to 30 atom chain of the segment: C—C, C—N, C—O, C—Si, C—S, S—N, and Si—O.

Alternatively, the transition metal complex can have reactive group(s) for immobilization or conjugation of the complexes to other substrates or carriers, examples of which include, but are not limited to, macromolecules (e.g., enzymes) and surfaces (e.g., electrode surfaces).

For reactive attachment to polymers, substrates, or other carriers, the transition metal complex precursor includes at least one reactive group that reacts with a reactive group on the polymer, substrate, or carrier. Typically, covalent bonds are formed between the two reactive groups to generate a linkage. Examples of such linkages are provided in Table 2, below. Generally, one of the reactive groups is an electrophile and the other reactive group is a nucleophile.

TABLE 2

Examples of Reactive Group Linkages

| First Reactive Group | Second Reactive Group | Resulting Linkage |
|---|---|---|
| Activated ester* | Amine | Carboxamide |
| Acrylamide | Thiol | Thioether |
| Acyl azide | Amine | Carboxamide |
| Acyl halide | Amine | Carboxamide |
| Carboxylic acid | Amine | Carboxamide |
| Aldehyde or ketone | Hydrazine | Hydrazone |
| Aldehyde or ketone | Hydroxyamine | Oxime |
| Alkyl halide | Amine | Alkylamine |
| Alkyl halide | Carboxylic acid | Carboxylic ester |
| Alkyl halide | Imidazole | Imidazolium |
| Alkyl halide | Pyridine | Pyridinium |
| Alkyl halide | Alcohol/phenol | Ether |

TABLE 2-continued

Examples of Reactive Group Linkages

| First Reactive Group | Second Reactive Group | Resulting Linkage |
|---|---|---|
| Alkyl halide | Thiol | Thioether |
| Alkyl sulfonate | Thiol | Thioether |
| Alkyl sulfonate | Pyridine | Pyridinium |
| Alkyl sulfonate | Imidazole | Imidazolium |
| Alkyl sulfonate | Alcohol/phenol | Ether |
| Anhydride | Alcohol/phenol | Ester |
| Anhydride | Amine | Carboxamide |
| Aziridine | Thiol | Thioether |
| Aziridine | Amine | Alkylamine |
| Aziridine | Pyridine | Pyridinium |
| Epoxide | Thiol | Thioether |
| Epoxide | Amine | Alkylamine |
| Epoxide | Pyridine | Pyridinium |
| Halotriazine | Amine | Aminotriazine |
| Halotriazine | Alcohol | Triazinyl ether |
| Imido ester | Amine | Amidine |
| Isocyanate | Amine | Urea |
| Isocyanate | Alcohol | Urethane |
| Isothiocyanate | Amine | Thiourea |
| Maleimide | Thiol | Thioether |
| Sulfonyl halide | Amine | Sulfonamide |

*Activated esters, as understood in the art, generally include esters of succinimidyl, benzotriazolyl, or aryl substituted by electron-withdrawing groups such as sulfo, nitro, cyano, or halo; or carboxylic acids activated by carbodiimides.

In some embodiments, the spacer includes a flexible linear chain of at least four atoms. Preferably, the flexible linear chain includes at least six or eight atoms, but less than about 30 atoms. More preferably, the number of atoms forming the flexible linear chain ranges from 8 to 18. In some instances, two or more flexible chains are included in the spacer. The flexible chain typically permits the spacer to move relative to the polymeric backbone, thereby allowing the transition metal complex on the end of the spacer to move. This is particularly useful for polymeric transition metal complexes that are used as redox mediators because the movement of the transition metal complex coupled by the spacer to the polymer backbone can facilitate transfer of electrons between transition metal complexes and with the electrode. This can enhance the electron transfer rate and can facilitate the desired electrochemical reaction at the electrode by, for example, improving the conduction lo of electrons by the crosslinked and hydrated polymer on the electrode.

In addition to the chains, the spacer can contain one or more other unsaturated groups. For example, the spacer can include an unsaturated functional group such as those listed in Table 1 under the heading "Resulting Linkage". As another example, the spacer can include a heterocycle or aryl group. For example, the spacer group of poly(4-vinylpyridine) or poly(N-vinylimidazole) would include a pyridine or imidazole functional group. In these specific instances, the heterocycle or aryl group is positioned between the flexible chain and the polymeric backbone, although this is not necessary to the invention.

Formula 17 schematically represent examples of the polymeric transition metal complexes of the present invention.

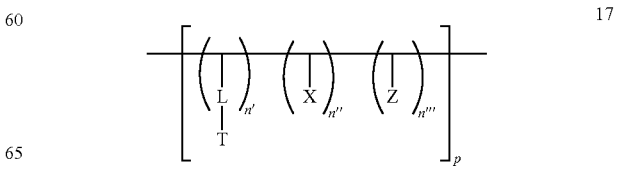

17

In general, the polymeric transition metal complex has a polymeric backbone with one or more types of pendant groups (represented in Formula 17 as L-T, X, and Z, respectively). The individual pendant groups, L-T, X, and Z, of each polymer unit can be ordered in any configuration. The number of polymer units is represent by p, which is an integer having a value of one or more. The product of p and (n'+n''+n''') is generally at least 5, preferably, at least 10, and can be 50 or more.

T is a transition metal complex as described above. L is a spacer group, as described above, and couples the transition metal complex, T, to the polymeric backbone. The number of spacer group-transition metal complex units (L-T) attached to the polymer backbone in each polymer unit is represented by n', which is an integer having a value of one or more.

X represents a pendant groups that does not contain a reactive substituent. The number of these pendant groups attached to the polymer backbone in each polymer unit is represented by n'', which is an integer having a value of zero or more.

Z represents a pendant group substituted with a reactive substituent that includes, but is not limited to, pyridyl, imidazolyl, carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photoreactive azido aryl groups. The pendant group, Z, can be used for cross-linking the polymer backbone during, for example, polymer immobilization on a surface. The number of these pendant groups attached to the polymer backbone in each polymer unit is represented by n''', which is an integer having a value of zero or more.

The polymeric transition metal complex typically has a weight average molecular weight of at least 5000, although in some instances lower molecular weight polymeric transition metal complexes can be used. The weight average molecular weight of the polymeric transition metal complex can be at least 10,000, 50,000, 100,000, or more and can depend on the application. This weight average molecular weight generally refers to the weight average molecular weight prior to crosslinking to form a film.

An example of a precursor polymer that can be used to form a polymeric transition metal complex is presented as Formula 18. This precursor polymer is poly(4-vinylpyridine) quaternized with an alkyl moiety substituted with a reactive group.

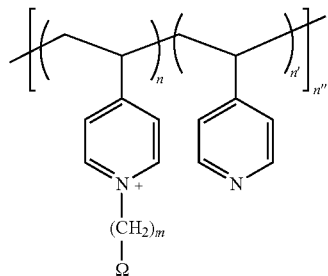

18 where Ω is the reactive group, m is typically 1 to 18, n and n' are the average numbers of pyridinium and pyridine subunits respectively in each repeating polymer unit, and n'' is the number of repeating polymer units.

Examples of polymeric transition metal complexes formed using this precursor polymer are illustrated by Formulas 19, 20 and 21:

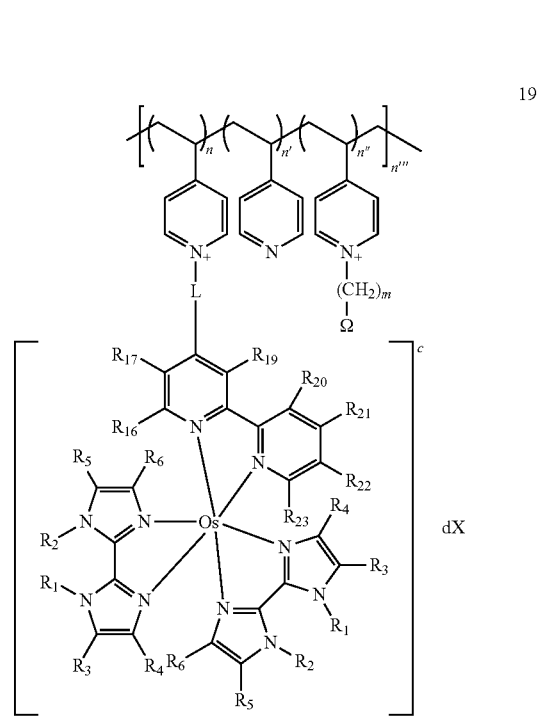

19

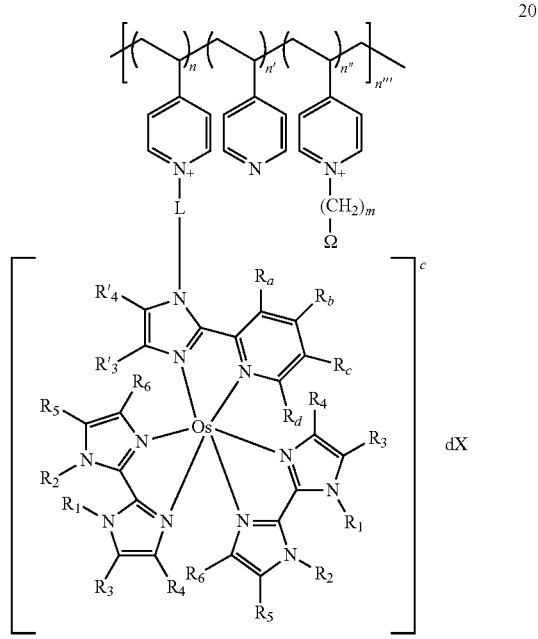

20

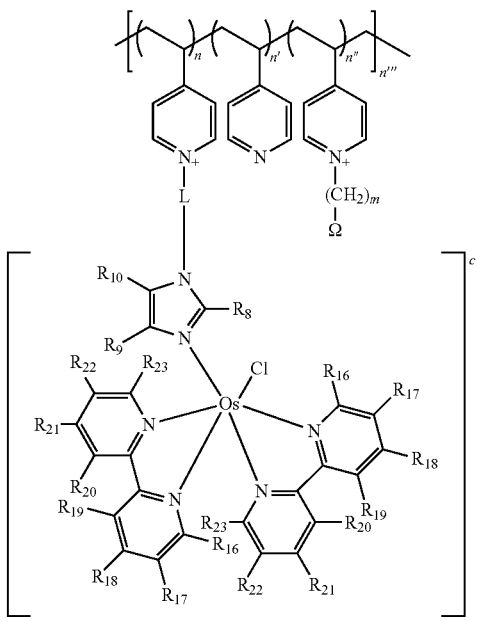

21

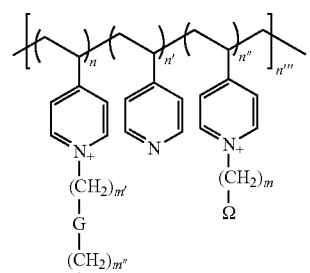

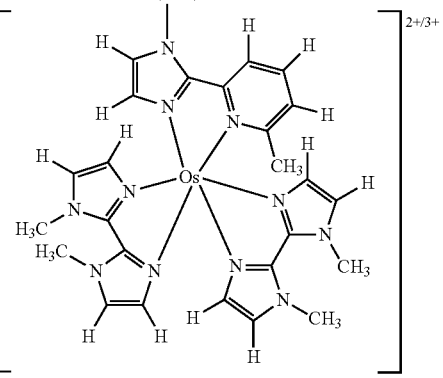

23 where Ω is the reactive group; m is 1 to 18; L is the spacer, as described above, formed by the reaction of the transition metal complex to the Ω; X represents counter ions; d represents the number of counter ions; c is an integer representing the charge of the complex; and $R_1$, $R_2$, $R_3$, $R_3$, $R_4$, $R_5$, $R_6$, $R_8$, $R_9$, $R_{10}$, $R_{16}$, $R_{17}$, $R_{18}$, $R_{19}$, $R_{20}$, $R_{21}$, $R_{22}$, $R_{23}$, $R'_3$, $R'_4$, $R_a$, $R_b$, $R_c$, and $R_d$ are as described above.

Specific examples of suitable polymeric transition metal complexes are illustrated in Formulas 22, 23, and 24.

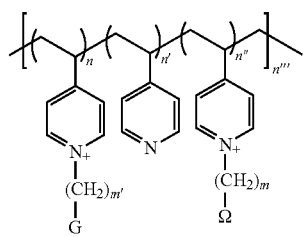

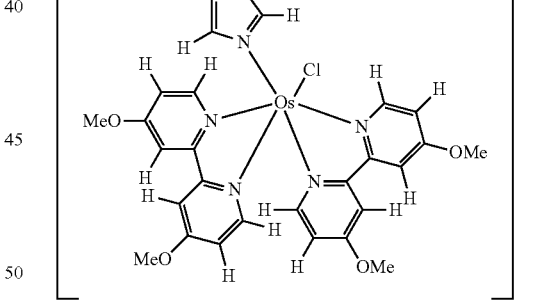

24

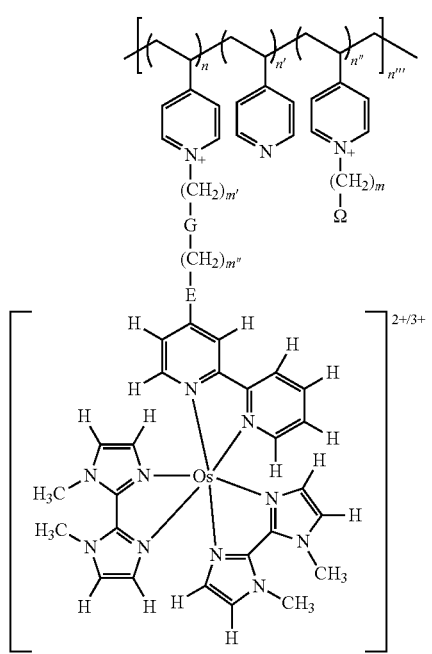

22 where G represents one of the "Resulting Linkages" of Table 1 such as, for example, an amide having the formula: —$CONR_{30}$— or —$NR_{30}CO$—, where $R_{30}$ is a hydrogen, methyl, ethyl or other 1 to 6 carbon alkyl. E is O, S or $NR_{31}$, where $R_{31}$ is hydrogen, methyl, ethyl or other 1 to 6 carbon alkyl. m' and m are the same and are typically in the range of 1 to 18 and m" is independently in the range of 1 to 18.

Transition metal complexes of the present invention can be soluble in water or other aqueous solutions, or in organic solvents. In general, the transition metal complexes can be made soluble in either aqueous or organic solvents by having an appropriate counter ion or ions, X. For example, transition metal complexes with small counter anions, such as $F^-$, $Cl^-$, and $Br^-$, tend to be water soluble. On the other hand, transition metal complexes with bulky counter anions, such as I⁻, $BF_4^-$ and $PF_6^-$, tend to be soluble in organic solvents. Preferably, the solubility of transition metal complexes of the present invention is greater than about 0.1 M (moles/liter) at 25° C. for a desired solvent.

The transition metal complexes discussed above are useful as redox mediators in electrochemical sensors for the detection of analytes in bio-fluids. The use of transition metal complexes as redox mediators is described, for example, in U.S. Pat. Nos. 5,262,035; 5,262,305; 5,320,725; 5,365,786; 5,593,852; 5,665,222; 5,972,199; and 6,143,164 and U.S. patent application Ser. No. 09/034,372, (now U.S. Pat. No. 6,134,461); Ser. No. 09/070,677, (now U.S. Pat. No. 6,175,752); Ser. No. 09/295,962, (now U.S. Pat. No. 6,338,790) and Ser. No. 09/434,026, all of which are herein incorporated by reference. The transitional metal complexes described herein can typically be used in place of those discussed in the references listed above. The transitions metal complexes that include a polymeric backbone and are redox mediators can also be referred to as "redox polymers The Sensor A sensor 42 includes at least one working electrode 58 formed on a substrate 50, as shown in FIG. 2. The sensor 42 may also include at least one counter electrode 60 (or counter/reference electrode) and/or at least one reference electrode 62 (see FIG. 8). The counter electrode 60 and/or reference electrode 62 may be formed on the substrate 50 or may be separate units. For example, the counter electrode and/or reference electrode may be formed on a second substrate which is also implanted in the patient or, for some embodiments of the implantable sensors, the counter electrode and/or reference electrode may be placed on the skin of the patient with the working electrode or electrodes being implanted into the patient. The use of an on-the-skin counter and/or reference electrode with an implantable working electrode is described in U.S. Pat. No. 5,593,852, incorporated herein by reference.

The working electrode or electrodes 58 are formed using conductive traces 52 disposed on the substrate 50. The counter electrode 60 and/or reference electrode 62, as well as other optional portions of the sensor 42, such as a temperature probe 66 (see FIG. 8), may also be formed using conductive traces 52 disposed on the substrate 50. These conductive traces 52 may be formed over a smooth surface of the substrate 50 or within channels 54 formed by, for example, embossing, indenting or otherwise creating a depression in the substrate 50.

A sensing layer 64 (see FIGS. 3A and 3B) is often formed proximate to or on at least one of the working electrodes 58 to facilitate the electrochemical detection of the analyte and the determination of its level in the sample fluid, particularly if the analyte cannot be electrolyzed at a desired rate and/or with a desired specificity on a bare electrode. The sensing layer 64 may include an electron transfer agent to transfer electrons directly or indirectly between the analyte and the working electrode 58. The sensing layer 64 may also contain a catalyst to catalyze a reaction of the analyte. The components of the sensing layer may be in a fluid or gel that is proximate to or in contact with the working electrode 58. Alternatively, the components of the sensing layer 64 may be disposed in a polymeric or sol-gel matrix that is proximate to or on the working electrode 58. Preferably, the components of the sensing layer 64 are non-leachably disposed within the sensor 42. More preferably, the components of the sensor 42 are immobilized within the sensor 42.

Figure 9:
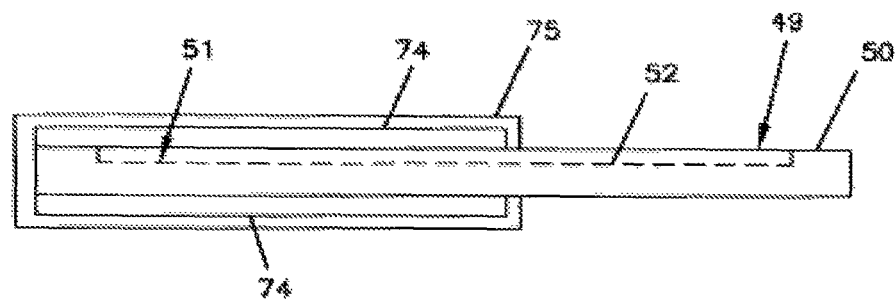
FIG. 9 is a side view of the analyte sensor of FIG. 2.
Figure 4A:
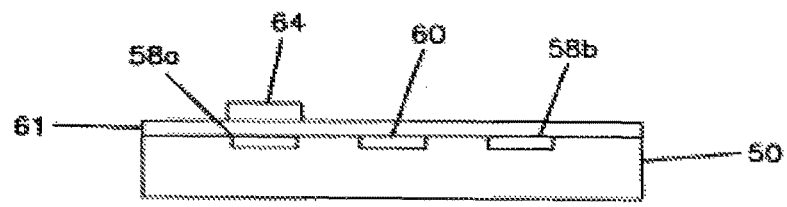
FIG. 4A is a cross-sectional view of a third embodiment of an analyte sensor, according to the invention.
Figure 4B:
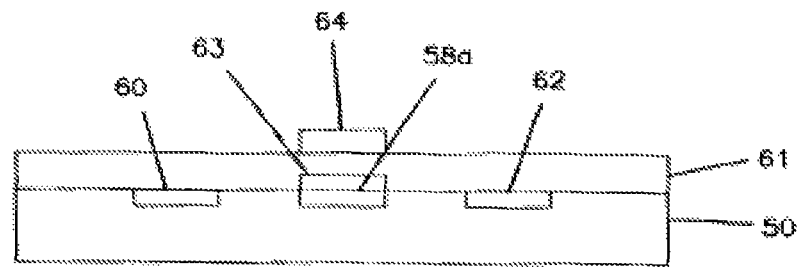
FIG. 4B is a cross-sectional view of a fourth embodiment of an analyte sensor, according to the invention.
Figure 5:
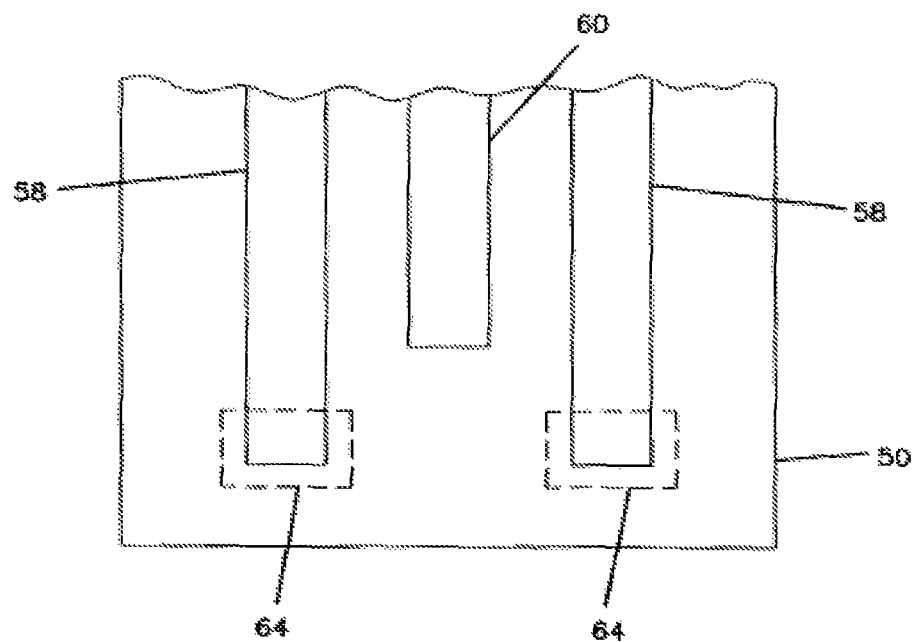
FIG. 5 is an expanded top view of a tip portion of the analyte sensor of FIG. 2.

In addition to the electrodes 58, 60, 62 and the sensing layer 64, the sensor 42 may also include a temperature probe 66 (see FIGS. 6 and 8), a mass transport limiting layer 74 (see FIG. 9), a biocompatible layer 75 (see FIG. 9), and/or other optional components, as described below. Each of these items enhances the functioning of and/or results from the sensor 42, as discussed below.

The Substrate

The substrate 50 may be formed using a variety of non-conducting materials, including, for example, polymeric or plastic materials and ceramic materials. Suitable materials for a particular sensor 42 may be determined, at least in part, based on the desired use of the sensor 42 and properties of the materials.

In some embodiments, the substrate is flexible. For example, if the sensor 42 is configured for implantation into a patient, then the sensor 42 may be made flexible (although rigid sensors may also be used for implantable sensors) to reduce pain to the patient and damage to the tissue caused by the implantation of and/or the wearing of the sensor 42. A flexible substrate 50 often increases the patient's comfort and allows a wider range of activities. Suitable materials for a flexible substrate 50 include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors 42 are made using a relatively rigid substrate 50 to, for example, provide structural support against bending or breaking. Examples of rigid materials that may be used as the substrate 50 include poorly conducting ceramics, such as aluminum oxide and silicon dioxide. One advantage of an implantable sensor 42 having a rigid substrate is that the sensor 42 may have a sharp point and/or a sharp edge to aid in implantation of a sensor 42 without an additional insertion device.

It will be appreciated that for many sensors 42 and sensor applications, both rigid and flexible sensors will operate adequately. The flexibility of the sensor 42 may also be controlled and varied along a continuum by changing, for example, the composition and/or thickness of the substrate 50.

In addition to considerations regarding flexibility, it is often desirable that implantable sensors 42 should have a substrate 50 which is non-toxic. Preferably, the substrate 50 is approved by one or more appropriate governmental agencies or private groups for in vivo use.

The sensor 42 may include optional features to facilitate insertion of an implantable sensor 42, as shown in FIG. 12. For example, the sensor 42 may be pointed at the tip 123 to ease insertion. In addition, the sensor 42 may include a barb 125 which assists in anchoring the sensor 42 within the tissue of the patient during operation of the sensor 42. However, the barb 125 is typically small enough that little damage is caused to the subcutaneous tissue when the sensor 42 is removed for replacement.

Although the substrate 50 in at least some embodiments has uniform dimensions along the entire length of the sensor 42, in other embodiments, the substrate 50 has a distal end 67 and a proximal end 65 with different widths 53, 55, respectively, as illustrated in FIG. 2. In these embodiments, the distal end 67 of the substrate 50 may have a relatively narrow width 53. For sensors 42 which are implantable into the subcutaneous tissue or another portion of a patient's body, the narrow width 53 of the distal end 67 of the substrate 50 may facilitate the implantation of the sensor 42.

Often, the narrower the width of the sensor 42, the less pain the patient will feel during implantation of the sensor and afterwards.

For subcutaneously implantable sensors 42 which are designed for continuous or periodic monitoring of the analyte during normal activities of the patient, a distal end 67 of the sensor 42 which is to be implanted into the patient has a width 53 of 2 mm or less, preferably 1 mm or less, and more preferably 0.5 mm or less. If the sensor 42 does not have regions of different widths, then the sensor 42 will typically have an overall width of, for example, 2 mm, 1.5 mm, 1 mm, 0.5 mm, 0.25 mm, or less. However, wider or narrower sensors may be used. In particular, wider implantable sensors may be used for insertion into veins or arteries or when the movement of the patient is limited, for example, when the patient is confined in bed or in a hospital.

Returning to FIG. 2, the proximal end 65 of the sensor 42 may have a width 55 larger than the distal end 67 to facilitate the connection between contact pads 49 of the electrodes and contacts on a control unit. The wider the sensor 42 at this point, the larger the contact pads 49 can be made. This may reduce the precision needed to properly connect the sensor 42 to contacts on the control unit (e.g., sensor control unit 44 of FIG. 1). However, the maximum width of the sensor 42 may be constrained so that the sensor 42 remains small for the convenience and comfort of the patient and/or to fit the desired size of the analyte monitor. For example, the proximal end 65 of a subcutaneously implantable sensor 42, such as the sensor 42 illustrated in FIG. 1, may have a width 55 ranging from 0.5 mm to 15 mm, preferably from 1 mm to 10 mm, and more preferably from 3 mm to 7 mm. However, wider or narrower sensors may be used in this and other in vivo applications.

The thickness of the substrate 50 may be determined by the mechanical properties of the substrate material (e.g., the strength, modulus, and/or flexibility of the material), the desired use of the sensor 42 including stresses on the substrate 50 arising from that use, as well as the depth of any channels or indentations formed in the substrate 50, as discussed below. Typically, the substrate 50 of a subcutaneously implantable sensor 42 for continuous or periodic monitoring of the level of an analyte while the patient engages in normal activities has a thickness of 50 to 500 µm and preferably 100 to 300 µm. However, thicker and thinner substrates 50 may be used, particularly in other types of in vivo sensors 42.

The length of the sensor 42 may have a wide range of values depending on a variety of factors. Factors which influence the length of an implantable sensor 42 may include the depth of implantation into the patient and the ability of the patient to manipulate a small flexible sensor 42 and make connections between the sensor 42 and the sensor control unit 44. A subcutaneously implantable sensor 42 for the analyte monitor illustrated in FIG. 1 may have a length ranging from 0.3 to 5 cm, however, longer or shorter sensors may be used. The length of the narrow portion of the sensor 42 (e.g., the portion which is subcutaneously inserted into the patient), if the sensor 42 has narrow and wide portions, is typically about 0.25 to 2 cm in length. However, longer and shorter portions may be used. All or only a part of this narrow portion may be subcutaneously implanted into the patient. The lengths of other implantable sensors 42 will vary depending, at least in part, on the portion of the patient into which the sensor 42 is to be implanted or inserted.

Conductive Traces

At least one conductive trace 52 is formed on the substrate for use in constructing a working electrode 58. In addition, other conductive traces 52 may be formed on the substrate 50 for use as electrodes (e.g., additional working electrodes, as well as counter, counter/reference, and/or reference electrodes) and other components, such as a temperature probe. The conductive traces 52 may extend most of the distance along a length 57 of the sensor 50, as illustrated in FIG. 2, although this is not necessary. The placement of the conductive traces 52 may depend on the particular configuration of the analyte monitoring system (e.g., the placement of control unit contacts and/or the sample chamber in relation to the sensor 42). For implantable sensors, particularly subcutaneously implantable sensors, the conductive traces typically extend close to the tip of the sensor 42 to minimize the amount of the sensor that must be implanted.

The conductive traces 52 may be formed on the substrate 50 by a variety of techniques, including, for example, photolithography, screen printing, or other impact or non-impact printing techniques. The conductive traces 52 may also be formed by carbonizing conductive traces 52 in an organic (e.g., polymeric or plastic) substrate 50 using a laser. A description of some exemplary methods for forming the sensor 42 is provided in U.S. patent application Ser. No. 09/034,422, incorporated herein by reference.

Figure 3A:
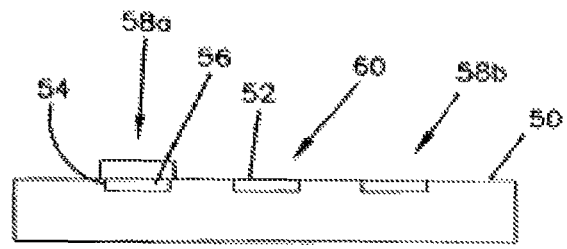
FIG. 3A is a cross-sectional view of the analyte sensor of FIG. 2.

Another method for disposing the conductive traces 52 on the substrate 50 includes the formation of recessed channels 54 in one or more surfaces of the substrate 50 and the subsequent filling of these recessed channels 54 with a conductive material 56, as shown in FIG. 3A. The recessed channels 54 may be formed by indenting, embossing, or otherwise creating a depression in the surface of the substrate 50. Exemplary methods for forming channels and electrodes in a surface of a substrate can be found in U.S. patent application Ser. No. 09/034,422. The depth of the channels is typically related to the thickness of the substrate 50. In one embodiment, the channels have depths in the range of about 12.5 to 75 µm (0.5 to 3 mils), and preferably about 25 to 50 µm (1 to 2 mils).

The conductive traces are typically formed using a conductive material 56 such as carbon (e.g., graphite), a conductive polymer, a metal or alloy (e.g., gold or gold alloy), or a metallic compound (e.g., ruthenium dioxide or titanium dioxide). The formation of films of carbon, conductive polymer, metal, alloy, or metallic compound are well-known and include, for example, chemical vapor deposition (CVD), physical vapor deposition, sputtering, reactive sputtering, printing, coating, and painting. The conductive material 56 which fills the channels 54 is often formed using a precursor material, such as a conductive ink or paste. In these embodiments, the conductive material 56 is deposited on the substrate 50 using methods such as coating, painting, or applying the material using a spreading instrument, such as a coating blade. Excess conductive material between the channels 54 is then removed by, for example, running a blade along the substrate surface.

In one embodiment, the conductive material 56 is a part of a precursor material, such as a conductive ink, obtainable, for example, from Ercon, Inc. (Wareham, Mass.), Metech, Inc. (Elverson, Pa.), E.I. du Pont de Nemours and Co. (Wilmington, Del.), Emca-Remex Products (Montgomeryville, Pa.), or MCA Services (Melbourn, Great Britain). The conductive ink is typically applied as a semiliquid or paste which contains particles of the carbon, metal, alloy, or metallic compound and a solvent or dispersant. After application of the conductive ink on the substrate 50 (e.g., in the channels 54), the solvent or dispersant evaporates to leave behind a solid mass of conductive material 56.

In addition to the particles of carbon, metal, alloy, or metallic compound, the conductive ink may also contain a binder. The binder may optionally be cured to further bind the conductive material 56 within the channel 54 and/or on the substrate 50. Curing the binder increases the conductivity of the conductive material 56. However, this is typically not necessary as the currents carried by the conductive material 56 within the conductive traces 52 are often relatively low (usually less than 1 µA and often less than 100 nA). Typical binders include, for example, polyurethane resins, cellulose derivatives, elastomers, and highly fluorinated polymers. Examples of elastomers include silicones, polymeric dienes, and acrylonitrile-butadiene-styrene (ABS) resins. One example of a fluorinated polymer binder is Teflon® (DuPont, Wilmington, Del.). These binders are cured using, for example, heat or light, including ultraviolet (UV) light. The appropriate curing method typically depends on the particular binder which is used.

Often, when a liquid or semiliquid precursor of the conductive material 56 (e.g., a conductive ink) is deposited in the channel 54, the precursor fills the channel 54. However, when the solvent or dispersant evaporates, the conductive material 56 which remains may lose volume such that the conductive material 56 may or may not continue to fill the channel 54. Preferred conductive materials 56 do not pull away from the substrate 50 as they lose volume, but rather decrease in height within the channel 54. These conductive materials 56 typically adhere well to the substrate 50 and therefore do not pull away from the substrate 50 during evaporation of the solvent or dispersant. Other suitable conductive materials 56 either adhere to at least a portion of the substrate 50 and/or contain another additive, such as a binder, which adheres the conductive material 56 to the substrate 50. Preferably, the conductive material 56 in the channels 54 is non-leachable, and more preferably immobilized on the substrate 50. In some embodiments, the conductive material 56 may be formed by multiple applications of a liquid or semiliquid precursor interspersed with removal of the solvent or dispersant.

In another embodiment, the channels 54 are formed using a laser. The laser carbonizes the polymer or plastic material. The carbon formed in this process is used as the conductive material 56. Additional conductive material 56, such as a conductive carbon ink, may be used to supplement the carbon formed by the laser.

In a further embodiment, the conductive traces 52 are formed by pad printing techniques. For example, a film of conductive material is formed either as a continuous film or as a coating layer deposited on a carrier film. This film of conductive material is brought between a print head and the substrate 50. A pattern on the surface of the substrate 50 is made using the print head according to a desired pattern of conductive traces 52. The conductive material is transferred by pressure and/or heat from the film of conductive material to the substrate 50. This technique often produces channels (e.g., depressions caused by the print head) in the substrate 50. Alternatively, the conductive material is deposited on the surface of the substrate 50 without forming substantial depressions.

In other embodiments, the conductive traces 52 are formed by non-impact printing techniques. Such techniques include electrophotography and magnetography. In these processes, an image of the conductive traces 52 is electrically or magnetically formed on a drum. A laser or LED may be used to electrically form an image. A magnetic recording head may be used to magnetically form an image. A toner material (e.g., a conductive material, such as a conductive ink) is then attracted to portions of the drum according to the image. The toner material is then applied to the substrate by contact between the drum and the substrate. For example, the substrate may be rolled over the drum. The toner material may then be dried and/or a binder in the toner material may be cured to adhere the toner material to the substrate.

Another non-impact printing technique includes ejecting droplets of conductive material onto the substrate in a desired pattern. Examples of this technique include ink jet printing and piezo jet printing. An image is sent to the printer which then ejects the conductive material (e.g., a conductive ink) according to the pattern. The printer may provide a continuous stream of conductive material or the printer may eject the conductive material in discrete amounts at the desired points.

Yet another non-impact printing embodiment of forming the conductive traces includes an ionographic process. In the this process, a curable, liquid precursor, such as a photopolymerizable acrylic resin (e.g., Solimer 7501 from Cubital, Bad Kreuznach, Germany) is deposited over a surface of a substrate 50. A photomask having a positive or negative image of the conductive traces 52 is then used to cure the liquid precursor. Light (e.g., visible or ultraviolet light) is directed through the photomask to cure the liquid precursor and form a solid layer over the substrate according to the image on the photomask. Uncured liquid precursor is removed leaving behind channels 54 in the solid layer. These channels 54 can then be filled with conductive material 56 to form conductive traces 52.

Conductive traces 52 (and channels 54, if used) can be formed with relatively narrow widths, for example, in the range of 25 to 250 µm, and including widths of, for example, 250 µm, 150 µm, 100 µm, 75 µm, 50 µm, 25 µm or less by the methods described above. In embodiments with two or more conductive traces 52 on the same side of the substrate 50, the conductive traces 52 are separated by distances sufficient to prevent conduction between the conductive traces 52. The edge-to-edge distance between the conductive traces is preferably in the range of 25 to 250 µm and may be, for example, 150 µm, 100 µm, 75 µm, 50 µm, or less. The density of the conductive traces 52 on the substrate 50 is preferably in the range of about 150 to 700 µm/trace and may be as small as 667 µm/trace or less, 333 µm/trace or less, or even 167 µm/trace or less.

The working electrode 58 and the counter electrode 60 (if a separate reference electrode is used) are often made using a conductive material 56, such as carbon. Suitable carbon conductive inks are available from Ercon, Inc. (Wareham, Mass.), Metech, Inc. (Elverson, Pa.), E.I. du Pont de Nemours and Co. (Wilmington, Del.), Emca-Remex Products (Montgomeryville, Pa.), or MCA Services (Melbourn, Great Britain). Typically, the working surface 51 of the working electrode 58 is at least a portion of the conductive trace 52 that is in contact with the analyte-containing fluid (e.g., implanted in the patient).

The reference electrode 62 and/or counter/reference electrode are typically formed using conductive material 56 that is a suitable reference material, for example silver/silver chloride or a non-leachable redox couple bound to a conductive material, for example, a carbon-bound redox couple. Suitable silver/silver chloride conductive inks are available from Ercon, Inc. (Wareham, Mass.), Metech, Inc. (Elverson, Pa.), E.I. du Pont de Nemours and Co. (Wilmington, Del.), Emca-Remex Products (Montgomeryville, Pa.), or MCA Services (Melbourn, Great Britain). Silver/silver chloride electrodes illustrate a type of reference electrode that involves the reaction of a metal electrode with a constituent of the sample or body fluid, in this case, Cl.sup.-.

Suitable redox couples for binding to the conductive material of the reference electrode include, for example, redox polymers (e.g., polymers having multiple redox centers.) It is preferred that the reference electrode surface be non-corroding so that an erroneous potential is not measured. Preferred conductive materials include less corrosive metals, such as gold and palladium. Most preferred are non-corrosive materials including non-metallic conductors, such as carbon and conducting polymers. A redox polymer can be adsorbed on or covalently bound to the conductive material of the reference electrode, such as a carbon surface of a conductive trace 52. Non-polymeric redox couples can be similarly bound to carbon or gold surfaces.

A variety of methods may be used to immobilize a redox polymer on an electrode surface. One method is adsorptive immobilization. This method is particularly useful for redox polymers with relatively high molecular weights. The molecular weight of a polymer may be increased, for example, by cross-linking.

Another method for immobilizing the redox polymer includes the functionalization of the electrode surface and then the chemical bonding, often covalently, of the redox polymer to the functional groups on the electrode surface. One example of this type of immobilization begins with a poly(4-vinylpyridine). The polymer's pyridine rings are, in part, complexed with a reducible/oxidizable species, such as $[Os(bpy)_2Cl]^{+/2+}$ where bpy is 2,2'-bipyridine. Part of the pyridine rings are quaternized by reaction with 2-bromoethylamine. The polymer is then crosslinked, for example, using a diepoxide, such as polyethylene glycol diglycidyl ether.

Carbon surfaces can be modified for attachment of a redox species or polymer, for example, by electroreduction of a diazonium salt. As an illustration, reduction of a diazonium salt formed upon diazotization of p-aminobenzoic acid modifies a carbon surface with phenylcarboxylic acid functional groups. These functional groups can then be activated by a carbodiimide, such as 1-ethyl-3-(3-dimethylaminopropyl)-carbodiimide hydrochloride. The activated functional groups are then bound with a amine-functionalized redox couple, such as the quaternized osmium-containing redox polymer described above or 2-aminoethylferrocene, to form the redox couple.

Similarly, gold can be functionalized by an amine, such as cystamine. A redox couple such as $[Os(bpy)_2(pyridine-4-carboxylate)Cl]^{0/+}$ is activated by 1-ethyl-3-(3-dimethylaminopropyl)-carbodiimide hydrochloride to form a reactive O-acylisourea which reacts with the gold-bound amine to form an amide.

In one embodiment, in addition to using the conductive traces 52 as electrodes or probe leads, two or more of the conductive traces 52 on the substrate 50 are used to give the patient a mild electrical shock when, for example, the analyte level exceeds a threshold level. This shock may act as a warning or alarm to the patient to initiate some action to restore the appropriate level of the analyte.

The mild electrical shock is produced by applying a potential between any two conductive traces 52 that are not otherwise connected by a conductive path. For example, two of the electrodes 58, 60, 62 or one electrode 58, 60, 62 and the temperature probe 66 may be used to provide the mild shock. Preferably, the working electrode 58 and the reference electrode 62 are not used for this purpose as this may cause some damage to the chemical components on or proximate to the particular electrode (e.g., the sensing layer on the working electrode or the redox couple on the reference electrode).

The current used to produce the mild shock is typically 0.1 to 1 mA. Higher or lower currents may be used, although care should be taken to avoid harm to the patient. The potential between the conductive traces is typically 1 to 10 volts. However, higher or lower voltages may be used depending, for example, on the resistance of the conductive traces 52, the distance between the conductive traces 52 and the desired amount of current. When the mild shock is delivered, potentials at the working electrode 58 and across the temperature probe 66 may be removed to prevent harm to those components caused by unwanted conduction between the working electrode 58 (and/or temperature probe 66, if used) and the conductive traces 52 which provide the mild shock.

Contact Pads

Typically, each of the conductive traces 52 includes a contact pad 49. The contact pad 49 may simply be a portion of the conductive trace 52 that is indistinguishable from the rest of the trace 52 except that the contact pad 49 is brought into contact with the conductive contacts of a control unit (e.g., the sensor control unit 44 of FIG. 1). More commonly, however, the contact pad 49 is a region of the conductive trace 52 that has a larger width than other regions of the trace 52 to facilitate a connection with the contacts on the control unit. By making the contact pads 49 relatively large as compared with the width of the conductive traces 52, the need for precise registration between the contact pads 49 and the contacts on the control unit is less critical than with small contact pads.

The contact pads 49 are typically made using the same material as the conductive material 56 of the conductive traces 52. However, this is not necessary. Although metal, alloys, and metallic compounds may be used to form the contact pads 49, in some embodiments, it is desirable to make the contact pads 49 from a carbon or other non-metallic material, such as a conducting polymer. In contrast to metal or alloy contact pads, carbon and other non-metallic contact pads are not easily corroded if the contact pads 49 are in a wet, moist, or humid environment. Metals and alloys may corrode under these conditions, particularly if the contact pads 49 and contacts of the control unit are made using different metals or alloys. However, carbon and non-metallic contact pads 49 do not significantly corrode, even if the contacts of the control device are metal or alloy.

One embodiment of the invention includes a sensor 42 having contact pads 49 and a control unit 44 having conductive contacts (not shown). During operation of the sensor 42, the contact pads 49 and conductive contacts are in contact with each other. In this embodiment, either the contact pads 49 or the conductive contacts are made using a non-corroding, conductive material. Such materials include, for example, carbon and conducting polymers. Preferred non-corroding materials include graphite and vitreous carbon. The opposing contact pad or conductive contact is made using carbon, a conducting polymer, a metal, such as gold, palladium, or platinum group metal, or a metallic compound, such as ruthenium dioxide. This configuration of contact pads and conductive contacts typically reduces corrosion. Preferably, when the sensor is placed in a 3 mM, and more preferably, in a 100 mM, NaCl solution, the signal arising due to the corrosion of the contact pads and/or conductive contacts is less than 3% of the signal generated by the sensor when exposed to concentration of analyte in the normal physiological range. For at least some subcutaneous glucose sensors, the current generated by analyte in a normal physiological range ranges from 3 to 500 nA.

Figure 11:
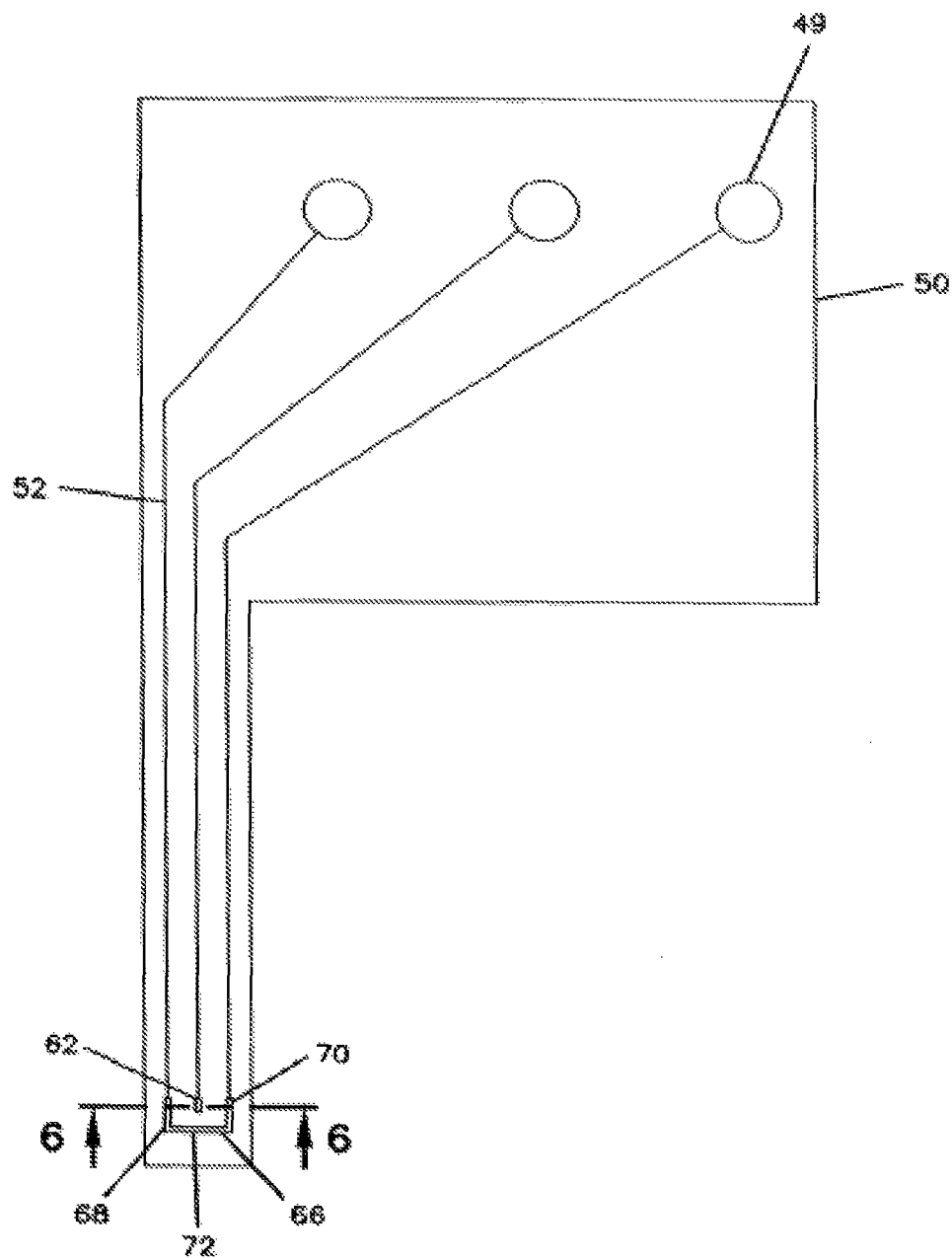
FIG. 11 is a bottom view of the analyte sensor of FIG. 6.

Each of the electrodes 58, 60, 62, as well as the two probe leads 68, 70 of the temperature probe 66 (described below), are connected to contact pads 49 as shown in FIGS. 10 and 11. In one embodiment (not shown), the contact pads 49 are on the same side of the substrate 50 as the respective electrodes or temperature probe leads to which the contact pads 49 are attached.

In other embodiments, the conductive traces 52 on at least one side are connected through vias in the substrate to contact pads 49a on the opposite surface of the substrate 50, as shown in FIGS. 10 and 11. An advantage of this configuration is that contact between the contacts on the control unit and each of the electrodes 58, 60, 62 and the probe leads 68, 70 of the temperature probe 66 can be made from a single side of the substrate 50.

In yet other embodiments (not shown), vias through the substrate are used to provide contact pads on both sides of the substrate 50 for each conductive trace 52. The vias connecting the conductive traces 52 with the contact pads 49a can be formed by making holes through the substrate 50 at the appropriate points and then filling the holes with conductive material 56.

Exemplary Electrode Configurations

Figure 3B:
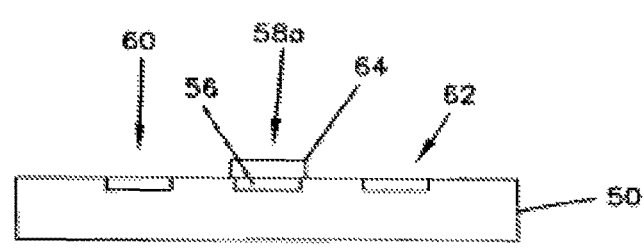
FIG. 3B is a cross-sectional view of another embodiment of an analyte sensor, according to the invention.

A number of exemplary electrode configurations are described below, however, it will be understood that other configurations may also be used. In one embodiment, illustrated in FIG. 3A, the sensor 42 includes two working electrodes 58a, 58b and one counter electrode 60, which also functions as a reference electrode. In another embodiment, the sensor includes one working electrode 58a, one counter electrode 60, and one reference electrode 62, as shown in FIG. 3B. Each of these embodiments is illustrated with all of the electrodes formed on the same side of the substrate 50.

Alternatively, one or more of the electrodes may be formed on an opposing side of the substrate 50. This may be convenient if the electrodes are formed using two different types of conductive material 56 (e.g., carbon and silver/silver chloride). Then, at least in some embodiments, only one type of conductive material 56 needs to be applied to each side of the substrate 50, thereby reducing the number of steps in the manufacturing process and/or easing the registration constraints in the process. For example, if the working electrode 58 is formed using a carbon-based conductive material 56 and the reference or counter/reference electrode is formed using a silver/silver chloride conductive material 56, then the working electrode and reference or counter/reference electrode may be formed on opposing sides of the substrate 50 for case of manufacture.

Figure 6:
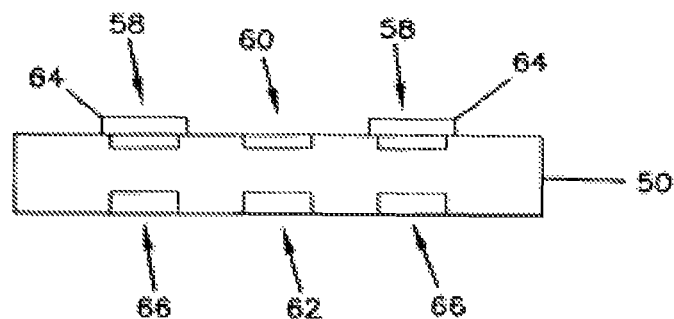
FIG. 6 is a cross-sectional view of a fifth embodiment of an analyte sensor, according to the invention.
Figure 7:
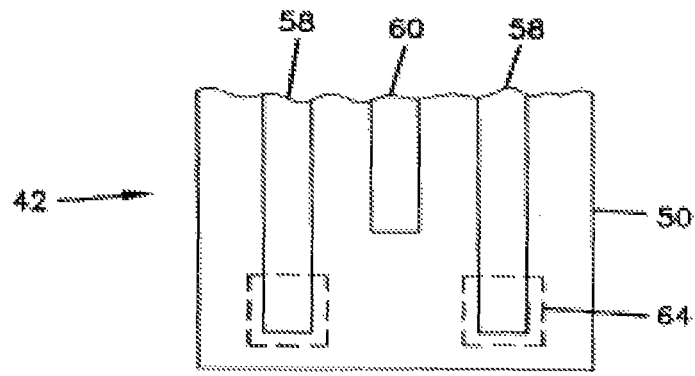
FIG. 7 is an expanded top view of a tip-portion of the analyte sensor of FIG. 6.
Figure 8:
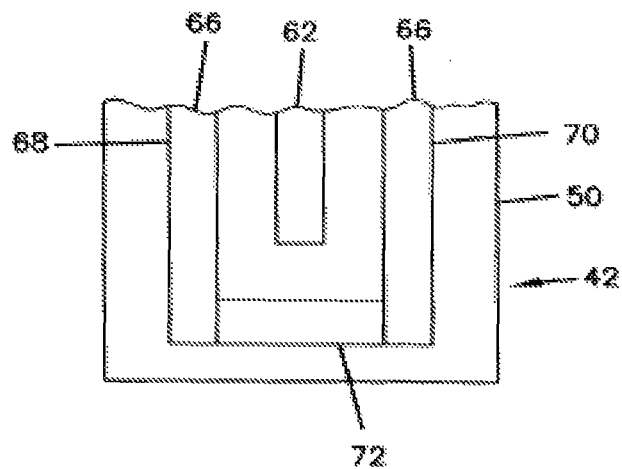
FIG. 8 is an expanded bottom view of a tip-portion of the analyte sensor of FIG. 6.

In another embodiment, two working electrodes 58 and one counter electrode 60 are formed on one side of the substrate 50 and one reference electrode 62 and a temperature probe 66 are formed on an opposing side of the substrate 50, as illustrated in FIG. 6. The opposing sides of the tip of this embodiment of the sensor 42 are illustrated in FIGS. 7 and 8.

In general, the redox mediator is disposed on or in proximity to (e.g., in a solution surrounding) a working electrode. The redox mediator transfers electrons between the working electrode and an analyte. In some preferred embodiments, an enzyme is also included to facilitate the transfer. For example, the redox mediator transfers electrons between the working electrode and glucose (typically via an enzyme) in an enzyme-catalyzed reaction of glucose. Redox polymers are particularly useful for forming non-leachable coatings on the working electrode. These can be formed, for example, by crosslinking the redox polymer on the working electrode, or by crosslinking the redox polymer and the enzyme on the working electrode Transition metal complexes can enable accurate, reproducible and quick or continuous assays. Transition metal complex redox mediators accept electrons from, or transfer electrons to, enzymes or analytes at a high rate and also exchange electrons rapidly with an electrode. Typically, the rate of self exchange, the process in which a reduced redox mediator transfers an electron to an oxidized redox mediator, is rapid. At a defined redox mediator concentration, this provides for more rapid transport of electrons between the enzyme (or analyte) and electrode, and thereby shortens the response time of the sensor. Additionally, the novel transition metal complex redox mediators are typically stable under ambient light and at the temperatures encountered in use, storage and transportation. Preferably, the transition metal complex redox mediators do not undergo chemical change, other than oxidation and reduction, in the period of use or under the conditions of storage, though the redox mediators can be designed to be activated by reacting, for example, with water or the analyte.

The transition metal complex can be used as a redox mediator in combination with a redox enzyme to electrooxidize or electroreduce the analyte or a compound derived of the analyte, for example by hydrolysis of the analyte. The redox potentials of the redox mediators are generally more positive (i.e. more oxidizing) than the redox potentials of the redox enzymes when the analyte is electrooxidized and more negative when the analyte is electroreduced. For example, the redox potentials of the preferred transition metal complex redox mediators used for electrooxidizing glucose with glucose oxidase or PQQ-glucose dehydrogenase as enzyme is between about −200 mV and +200 mV versus a Ag/AgCl reference electrode, and the most preferred mediators have redox potentials between about −100 mV and about +100 mV versus a Ag/AgCl reference electrode Crosslinking in Transition Metal Complex Polymers Electron transport involves an exchange of electrons between segments of the redox polymers (e.g., one or more transition metal complexes coupled to a polymeric backbone, as described above) in a crosslinked film disposed on an electrode. The transition metal complex can be bound to the polymer backbone though covalent, coordinative or ionic bonds, where covalent and coordinative binding are preferred. Electron exchange occurs, for example, through the collision of different segments of the crosslinked redox polymer. Electrons transported through the redox polymer can originate from, for example, electrooxidation or electroreduction of an enzymatic substrate, such as, for example, the oxidation of glucose by glucose oxidase.

The degree of crosslinking of the redox polymer can influence the transport of electrons or ions and thereby the rates of the electrochemical reactions. Excessive crosslinking of the polymer can reduce the mobility of the segments of the redox polymer. A reduction in segment mobility can slow the diffusion of electrons or ions through the redox polymer film. A reduction in the diffusivity of electrons, for example, can require a concomitant reduction in the thickness of the film on the electrode where electrons or electron vacancies are collected or delivered. The degree of crosslinking in a redox polymer film can thus affect the transport of electrons from, for example, an enzyme to the transition metal redox centers of the redox polymer such as, for example, $Os^{2+/3+}$ metal redox centers; between redox centers of the redox polymer; and from these transition metal redox centers to the electrode.

Inadequate crosslinking of a redox polymer can result in excessive swelling of the redox polymer film and to the leaching of the components of the redox polymer film. Excessive swelling can also result in the migration of the swollen polymer into the analyzed solution, in the softening of the redox polymer film, in the film's susceptibility to removal by shear, or any combination of these effects.

Crosslinking can decrease the leaching of film components and can improve the mechanical stability of the film under shear stress. For example, as disclosed in Binyamin, G. and Heller, A; *Stabilization of Wired Glucose Oxidase Anodes Rotating at 1000 rpm at 37°C.*; Journal of the Electrochemical Society, 146(8), 2965-2967, 1999, herein incorporated by reference, replacing a difunctional crosslinker, such as polyethylene glycol diglycidyl ether, with a trifunctional crosslinker such as N,N-diglycidyl-4-glycidyloxyaniline, for example, can reduce leaching and shear problems associated with inadequate crosslinking.

Examples of other bifunctional, trifunctional and tetrafunctional crosslinkers are listed below:

polymers is the increased mobility of the pendant transition metal complexes, resulting from the flexibility of the pendant groups. As a result, in at least some embodiments, fewer transition metal complexes per polymer backbone are needed to achieve a desired level of diffusivity of electrons and current density of analyte electrooxidation or electroreduction.

Coordination in Transition Metal Complex Polymers

Transition metal complexes can be directly or indirectly attached to a polymeric backbone, depending on the availability and nature of the reactive groups on the complex and the polymeric backbone. For example, the pyridine groups in poly(4-vinylpyridine) or the imidazole groups in poly(N-vinylimidazole) are capable of acting as monodentate ligands and thus can be attached to a metal center directly. Alternatively, the pyridine groups in poly(4-vinylpyridine) or the imidazole groups in poly(N-vinylimidazole) can be quaternized with a substituted alkyl moiety having a suitable reactive group, such as a carboxylate function, that can be activated to form a covalent bond with a reactive group, such

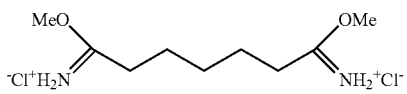

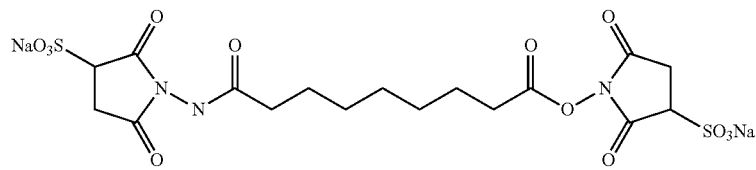

Amine-reactive Bifunctional Crosslinkers

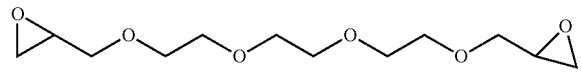

Pyridine- or Imidazole-reactive Bifunctional Crosslinkers

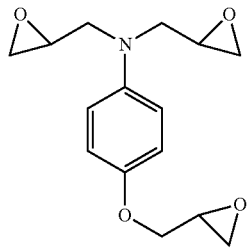

Pyridine- or Imidazole-reactive trifunctional Crosslinkers

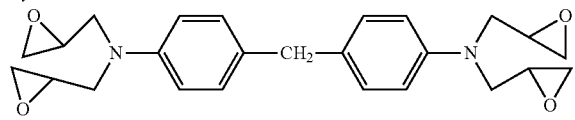

Pyridine- or Imidazole-reactive Tetrafunctional Crosslinkers

Alternatively, the number of crosslinking sites can be increased by reducing the number of transition metal complexes attached to the polymeric backbone, thus making more polymer pendant groups available for crosslinking. One important advantage of at least some of the redox as an amine, of the transition metal complex. (See Table 2 for a list of other examples of reactive groups.)

Redox centers such as, for example, $Os^{2+/3+}$ can be coordinated with five heterocyclic nitrogens and an additional ligand such as, for example, a chloride anion. An example of such a coordination complex includes two bipyridine ligands which form stable coordinative bonds, the pyridine of poly(4-vinylpyridine) which forms a weaker coordinative bond, and a chloride anion which forms the least stable coordinative bond.

Alternatively, redox centers, such as $Os^{2+/3+}$, can be coordinated with six heterocyclic nitrogen atoms in its inner coordination sphere. The six coordinating atoms are preferably paired in the ligands, for example, each ligand is composed of at least two rings. Pairing of the coordinating atoms can influence the potential of an electrode used in conjunction with redox polymers of the present invention.

Typically, for analysis of glucose, the potential at which the working electrode, coated with the redox polymer, is poised is negative of about +250 mV vs. SCE (standard calomel electrode). Preferably, the electrode is poised negative of about +150 mV vs. SCE. Poising the electrode at these potentials reduces the interfering electrooxidation of constituents of biological solutions such as, for example, urate, ascorbate and acetaminophen. The potential can be modified by altering the ligand structure of the complex.

The redox potential of a redox polymer, as described herein, is related to the potential at which the electrode is poised. Selection of a redox polymer with a desired redox potential allows tuning of the potential at which the electrode is best poised. The redox potentials of a number of the redox polymers described herein are negative of about +150 mV vs. SCE and can be negative of about +50 mV vs. SCE to allow the poising of the electrode potentials negative of about +250 mV vs. SCE and preferably negative of about +150 mV vs. SCE.

The strength of the coordination bond can influence the potential of the redox centers in the redox polymers. Typically, the stronger the coordinative bond, the more positive the redox potential. A shift in the potential of a redox center resulting from a change in the coordination sphere of the transition metal can produce a labile transition metal complex. For example, when the redox potential of an $Os^{2+/3+}$ complex is downshifted by changing the coordination sphere, the complex becomes labile. Such a labile transition metal complex may be undesirable when fashioning a metal complex polymer for use as a redox mediator and can be avoided through the use of weakly coordinating multidentate or chelating heterocyclics as ligands.

Electrode Interference

Transition metal complexes used as redox mediators in electrodes can be affected by the presence of transition metals in the analyzed sample including, for example, $Fe^{3+}$ or $Zn^{2+}$. The addition of a transition metal cation to a buffer used to test an electrode results in a decline in the current produced. The degree of current decline depends on the presence of anions in the buffer which precipitate the transition metal cations. The lesser the residual concentration of transition metal cations in the sample solution, the more stable the current. Anions which aid in the precipitation of transition metal cations include, for example, phosphate. It has been found that a decline in current upon the addition of transition metal cations is most pronounced in non-phosphate buffers. If an electrode is transferred from a buffer containing a transition metal cation to a buffer substantially free of the transition metal cation, the original current is restored.

The decline in current is thought to be due to additional crosslinking of a pyridine-containing polymer backbone produced by the transition metal cations. The transition metal cations can coordinate nitrogen atoms of different chains and chain segments of the polymers. Coordinative crosslinking of nitrogen atoms of different chain segments by transition metal cations can reduce the diffusivity of electrons.

Serum and other physiological fluids contain traces of transition metal ions, which can diffuse into the films of electrodes made with the redox polymers of the present invention, lowering the diffusivity of electrons and thereby the highest current reached at high analyte concentration. In addition, transition metal ions like iron and copper can bind to proteins of enzymes and to the reaction centers or channels of enzymes, reducing their turnover rate. The resulting decrease in sensitivity can be remedied through the use of anions which complex with interfering transition metal ions, for example, in a buffer employed during the production of the transition metal complex. A non-cyclic polyphosphate such as, for example, pyrophosphate or triphosphate, can be used. For example, sodium or potassium non-cyclic polyphosphate buffers can be used to exchange phosphate anions for those anions in the transition metal complex which do not precipitate transition metal ions. The use of linear phosphates can alleviate the decrease in sensitivity by forming strong complexes with the damaging transition metal ions, assuring that their activity will be low. Other complexing agents can also be used as long as they are not electrooxidized or electroreduced at the potential at which the electrode is poised.

Enzyme Damage and its Alleviation

Glucose oxidase is a flavoprotein enzyme that catalyzes the oxidation by dioxygen of D-glucose to D-glucono-1,5-lactone and hydrogen peroxide. Reduced transition metal cations such as, for example, $Fe^{2+}$, and some transition metal complexes, can react with hydrogen peroxide. These reactions form destructive OH radicals and the corresponding oxidized cations. The presence of these newly formed transition metal cations can inhibit the enzyme and react with the metal complex. Also, the oxidized transition metal cation can be reduced by the $FADH_2$ centers of an enzyme, or by the transition metal complex.

Inhibition of the active site of an enzyme or a transition metal complex by a transition metal cation, as well as damaging reactions with OH radicals can be alleviated, thus increasing the sensitivity and functionality of the electrodes by incorporating non-cyclic polyphosphates, as discussed above. Because the polyphosphate/metal cation complex typically has a high (oxidizing) redox potential, its rate of oxidation by hydrogen peroxide is usually slow. Alternatively, an enzyme such as, for example, catalase, can be employed to degrade hydrogen peroxide.

EXAMPLES

Unless indicated otherwise, all of the chemical reagents are available from Aldrich Chemical Co. (Milwaukee, Wis.) or other sources. Additional examples are provided in U.S. Pat. No. 6,605,200 entitled "Polymeric Transition Metal Complexes and Uses Thereof", incorporated herein by reference. For purposes of illustration, the synthesis of several transition metal complex ligands are shown below:

Example 1

Synthesis of 4-(5-carboxypentyl)amino-2,2'-bipyridyl

This example illustrates how a carboxy reactive group is introduced onto a 2.2'-bipyridyl derivative.

Synthesis of compound D: To compound C (formed from A and B according to

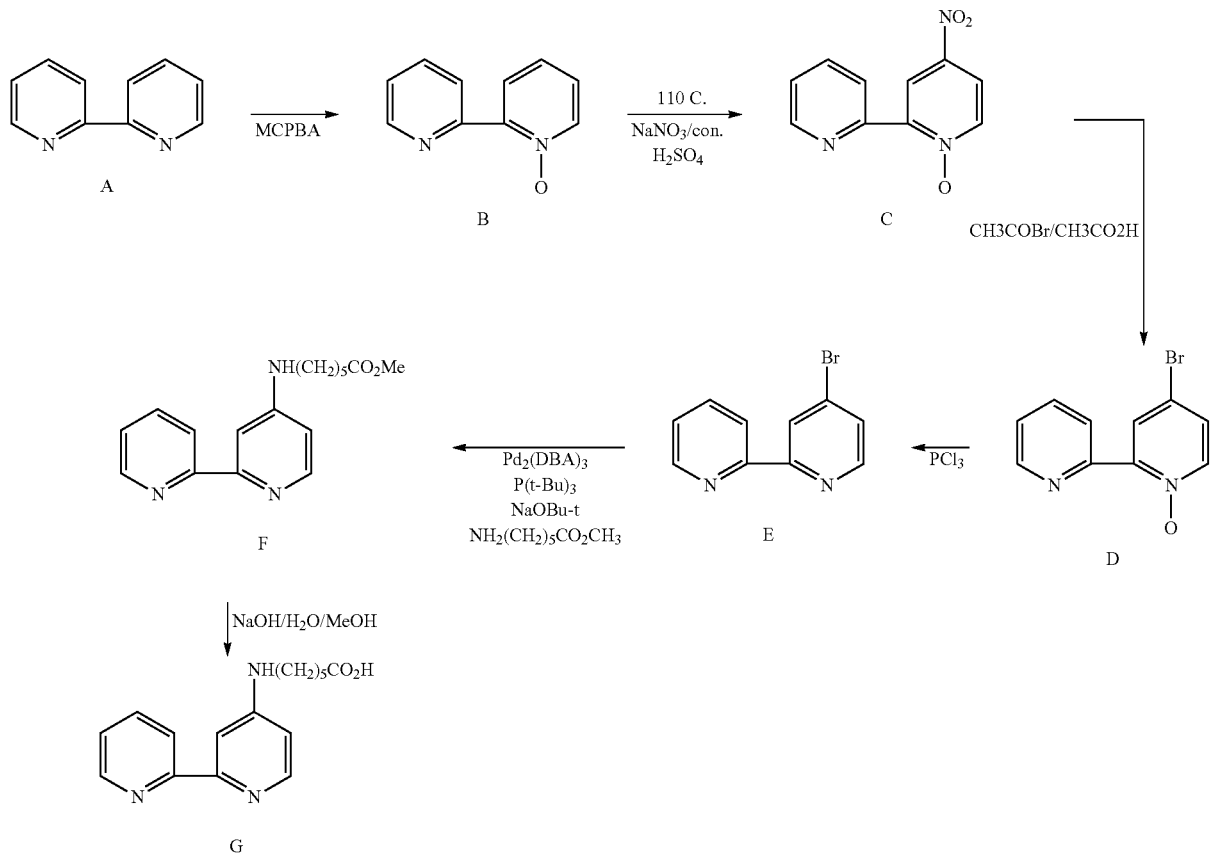

Wenkert, D.; Woodward, R. B. *J. Org. chem.* 48, 283(1983)) (5 g) dissolved in 30 mL acetic acid in a 100 ml round bottom flask was added 16 mL acetyl bromide. The yellow mixture was refluxed for 1.5 h and then rotovaporated to dryness. The resulting light yellow solid of D was sufficiently pure enough for the next step without further purification. Yield: 95%

Synthesis of compound E: To a stirred suspension of compound D in 60 mL CHCl$_3$ was added 12 mL PCl$_3$ at room temperature. The mixture was refluxed for 2 h under N$_2$ and then cooled to room temperature. The reaction mixture was poured into 100 mL ice/water. The aqueous layer was separated and saved. The CHCl$_3$ layer was extracted three times with H$_2$O (3×60 mL) and then discarded. The combined aqueous solution was neutralized with NaHCO$_3$ powder to about pH 7 to 8. The resulting white precipitate was collected by suction filtration, washed with H$_2$O (30 mL) and then dried under vacuum at 50° C. for 24 h. Yield: 85%.

Synthesis of compound F: Compound F was synthesized from compound E (5 g) and 6-aminocaproic acid methyl ester (6 g) using the palladium-catalyzed amination method of aryl bromides described by Hartwig et al. (Hartwig, J. F., et al. *J. Org. Chem.* 64, 5575 (1999)). Yield: 90%.

Synthesis of compound G: Compound F (3 g) dissolved in 20 mL MeOH was added to a solution of NaOH (0.6 g) in 30 mL H$_2$O. The resulting solution was stirred at room temperature for 24 h and then neutralized to pH 7 with dilute HCl. The solution was saturated with NaCl and then extracted with CHCl$_3$. The CHCl$_3$ extract was evaporated to dryness and then purified by a silica gel column eluted with 10% H$_2$O/CH$_3$CN. Yield: 70%.

Example 2

Synthesis of a 4-((6-Aminohexyl)amino)-2,2'-bipyridine

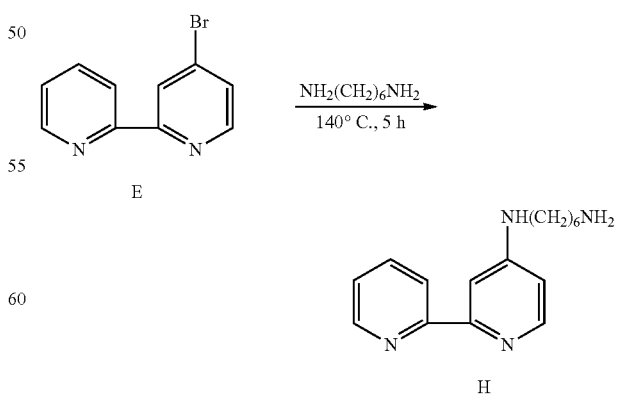

This example illustrates the general synthesis of a 2,2'-bipyridyl with an amine reactive group.

Synthesis of compound H: A mixture of compound E (2.5 g) and 1,6-diaminohexane (15 g) in a 250 mL round bottom flask was heated under $N_2$ at 140° C. in an oil bath for 4-5 h. Excess 1,6-diaminohexane was removed by high vacuum distillation at 90-120° C. The product was purified by a silica gel column, eluting with 5% $NH_4OH$ in isopropyl alcohol. Yield: 70%.

Example 3

Synthesis of 1,1'-dimethyl-2,2'-biimidazole

This example illustrates the synthesis of 2,2'-biimidazole derivatives.

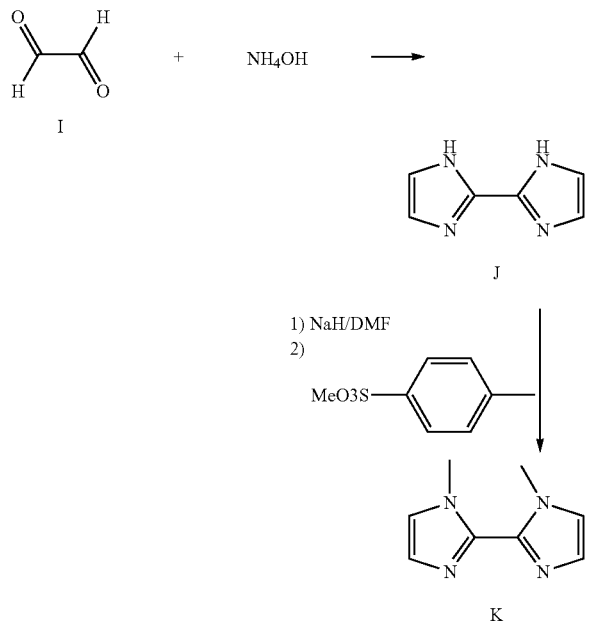

The alkylation step can be carried out stepwise so two different alkyl groups can be introduced. For example:

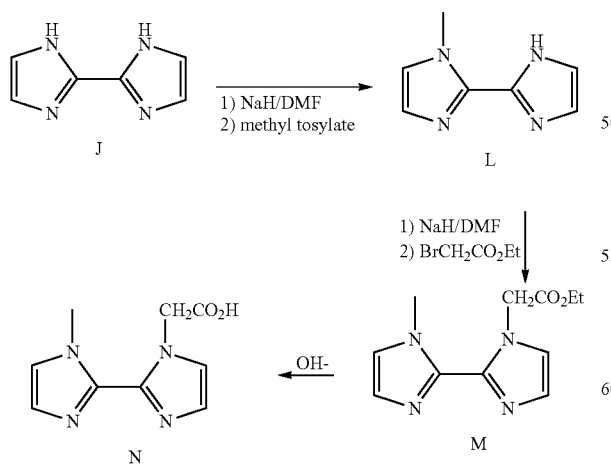

Synthesis of compound K: To a stirred solution of compound J (formed from I according to Fieselmann, B. F., et al. *Inorg. Chem.* 17, 2078(1978)) (4.6 g, 34.3 mmoles) in 100 mL dry DMF in a 250 ml round bottom flask cooled in an ice/water bath was added in portions NaH (60% in mineral oil, 2.7 g, 68.6 mmoles). After the solution was stirred at 0° C. for one more hour under $N_2$, methyl toluenesulfonate (10.3 mL, 68.6 mmoles) was added in small portions using a syringe over 30 min. The stirring of the solution in the ice/water bath was continued for 1 h and then at room temperature for 3 h. The solvent was removed by vacuum distillation. The dark residue was triturated with ether and then suction filtered and dried under vacuum. The product was purified by sublimation. Yield: 80%.

Synthesis of compound L: Compound L was prepared using the method described for the synthesis of compound K except that only one equivalent each of compound J, NaH and methyl toluenesulfonate was used. The product was purified by sublimation.

Synthesis of compound M: To a stirred solution of compound L (1 g, 6.8 mmoles) in 20 mL dry DMF in a 50 ml round bottom flask cooled in a ice/water bath is added in portions NaH (60% in mineral oil, 0.27 g, 6.8 mmoles). After the solution is stirred at 0° C. for one more hour under $N_2$, ethyl bromoacetate (0.75 mL, 6.8 mmoles) is added in small portions via a syringe over 15 min. The stirring of the solution is continued in the ice/water bath for 1 h and then at room temperature for 3 h. The solvent is removed by vacuum distillation. The product is purified by a silica gel column using 10% $MeOH/CHCl_3$ as the eluent.

Synthesis of Compound N: Compound M (1 g) is hydrolyzed using the method described for the synthesis of compound G. The product is purified by a silica gel column using 10% $H_2O/CH_3CN$ as the eluent.

Example 4

Synthesis of 2-(2-Pyridyl)imidazole Heterobidentate Ligands

This example illustrates a general synthesis of heterobidentate ligands containing an imidazole ring.

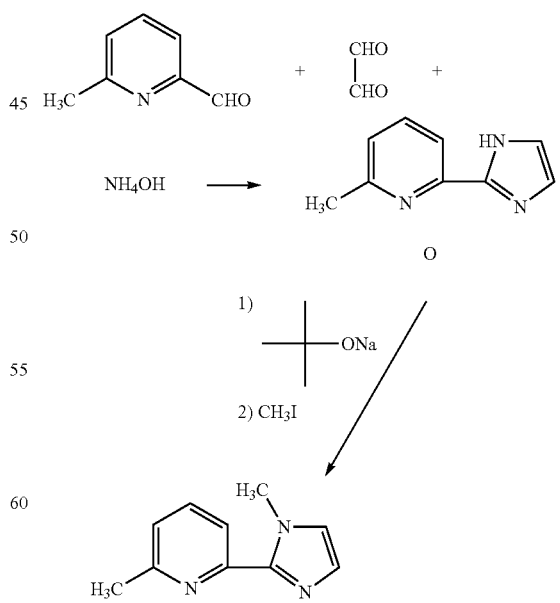

Synthesis of compound O: A solution of 6-methylpyridine-2-carboxaldehyde (26 g, 0.21 mole) and glyoxal (40%, 30 mL) in 50 mL EtOH in a three-necked 250 mL round bottom flask fitted with a thermometer and an addition funnel was stirred in a NaCl/ice bath. When the solution was cooled to below 5° C., conc. NH$_4$OH was added dropwise through the addition funnel. The rate of the addition was controlled so that the temperature of the solution was maintained at below 5° C. After the addition, the stirring of the yellow solution was continued in the ice bath for 1 h and then at room temperature overnight. The light yellow crystals were collected by suction filtration and washed with H$_2$O (20 mL). The crystals were resuspended in H$_2$O (200 mL) and boiled briefly, followed by suction filtration, to collect the product which was dried under high vacuum. Yield: 35%.

Synthesis of compound P: Sodium t-butoxide (2 g, 20.8 mmoles) was added in one portion to a stirred solution of compound O (3 g, 18.9 mmoles) in 50 mL dry DMF. After all of the sodium t-butoxide was dissolved, iodomethane (1.3 mL) was added dropwise using a syringe. The stirring of the solution was continued at room temperature for 2 h and then the solution was poured into H$_2$O (150 mL). The product was extracted with EtOAc, and the extract was dried with anhydrous Na$_2$SO$_4$ and then evaporated to give crude compound P. The product was purified by separation on a silica gel column using 10% MeOH/CHCl$_3$ as the eluent. Yield: 70%.

Synthesis of compound Q: Ammonium hexachloroosmate (200 mg, 0.46 mmoles) and compound K (221 mg, 1.37 mmoles) were mixed in 15 mL ethylene glycol in a 100 mL three-necked round bottom flask fitted with a reflux condenser. The mixture was degassed with N$_2$ for 15 min and then stirred under N$_2$ at 200-210° C. for 24 hrs. The solvent was removed by high vacuum distillation at 90-100° C. The green colored crude product was dissolved in 15 mL H$_2$O and stirred in air to be fully oxidized to the dark blue colored Os(III) oxidation state (about 24 h). The product was purified on a LH-20 reverse phase column using H$_2$O as the eluent. Yield: 50%.

Example 6

Synthesis of Transition Metal Complexes with Mixed Ligands

Transition metal complexes containing multiple types of ligands can be synthesized stepwise. First, a transition metal complex intermediate that contains one desired type of ligand and halide ligand(s), for example, chloride, is synthesized. Then the intermediate is subjected to a ligand substitution reaction to displace the halide ligand(s) with another desired type of ligand. The preparation of the following osmium complex illustrates the general synthetic scheme.

Example 5

Synthesis of Transition Metal Complexes with Multiple Identical Ligands

Transition metal complexes containing multiple identical bidentate or tridentate ligands can be synthesized in one step from a metal halide salt and the ligand. This example illustrates the synthesis of an osmium complex with three identical 2,2'-biimidazole bidentate ligands.

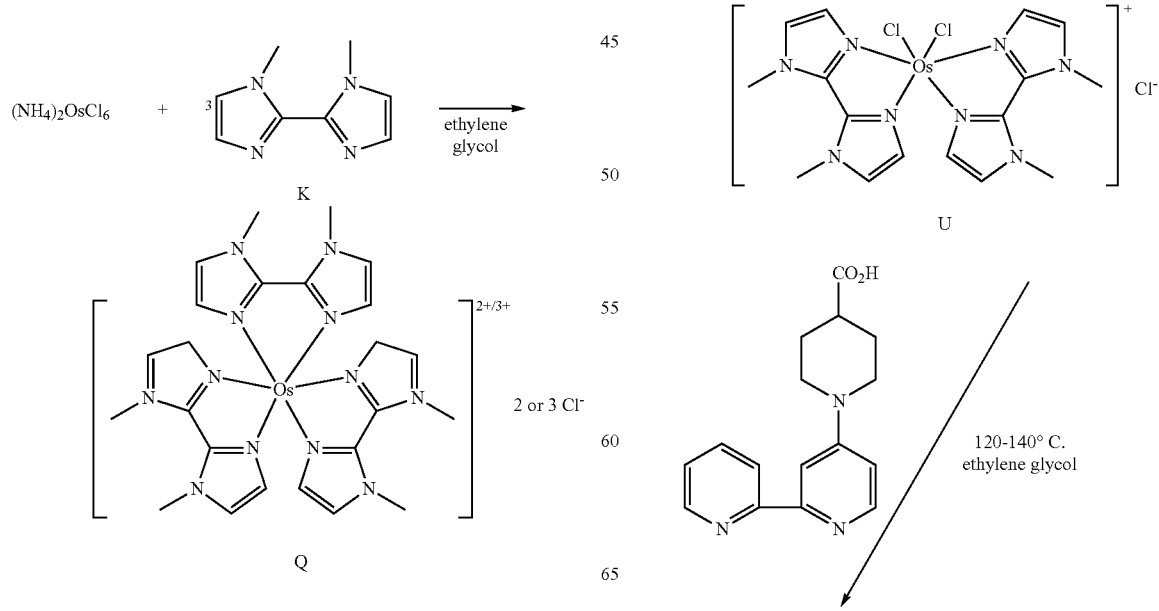

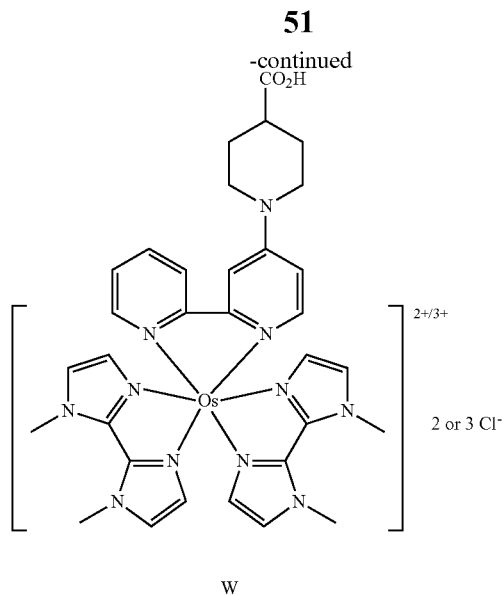

W

Synthesis of Compound U: Potassium hexachloroosmate (1 g, 2.08 mmoles), compound K (0.67 g, 4.16 mmoles) and LiCl (1 g, 23.8 mmoles) were suspended in 40 mL ethylene glycol in a 250 mL three-necked round bottom flask fitted with a reflux condenser. The suspension was degassed with $N_2$ for 15 min and then stirred under $N_2$ at 170° C. in an oil bath for 7-8 h, resulting in a dark brown solution. The solvent was removed by high vacuum distillation at 90-100° C. bath temperature. The gummy solid was triturated with acetone twice (2×50 mL) and then with $H_2O$ once (50 mL). The product was dried at 50° C. under high vacuum for 24 h.

Synthesis of compound W: A suspension of compound U (119 mg, 0.192 mmole) and 4-(4-carboxypiperidino)amino-2,2'-bipyridyl (prepared from compound E and ethyl isonipecotate using the synthetic methods for compounds F and G) was made in 10 mL ethylene glycol in a 100 mL three-necked round bottom flask equipped with a reflux condenser. The suspension was degassed with $N_2$ for 15 min and then stirred under $N_2$ at 130° C. in an oil bath for 24 h. The dark brown solution was cooled to room temperature and then poured into EtOAc (50 mL). The precipitate was collected by suction filtration. The dark brown solid thus obtained was compound W with osmium in a 2+ oxidation state. For ease of purification, the osmium 2+ complex was oxidized to an osmium 3+ complex by dissolving the dark brown solid in 20 mL $H_2O$ and stirring the solution in open air for 24 h. The resulting dark green solution was poured into a stirred solution of $NH_4PF_6$ (1 g) in 20 mL $H_2O$. The resulting dark green precipitate of [Os(1,1'-dimethyl-2,2'-biimidazole)$_2$(4-(4-carboxypiperidino)amino-2,2'-bipyridyl)]$^{3+}$3$PF_6^-$ was collected by suction filtration and washed with 5 mL $H_2O$ and then dried at 40° C. under high vacuum for 48 h. The counter anion $PF_6^-$ of [Os(1,1'-dimethyl-2,2'-biimidazole)$_2$(4-(4-carboxypiperidino)amino-2,2'-bipyridyl)]$^{3+}$3$PF_6^-$ was exchanged to the more water soluble chloride anion. A suspension of the $PF_6^-$ salt of compound W (150 mg) and Cl$^-$ resin (10 mL) in $H_2O$ (20 mL) was stirred for 24 h, at the end of which period all of osmium complex was dissolved. The dark green solution was separated by suction filtration and then lyophilized to give compound W.

Synthesis of [Os(4,4'-dimethoxy-2'2'-bipyridyl)$_2$(1-(3-aminopropyl)imidazole)]Cl$_3$

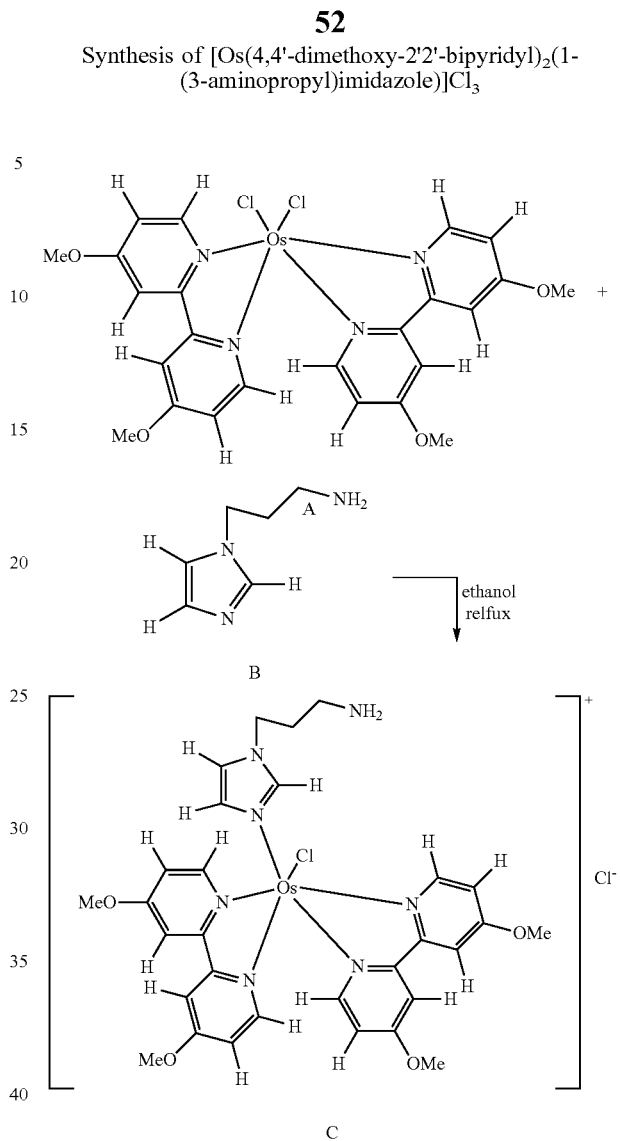

A suspension of compound A (prepared according to U.S. Pat. No. 5,393,903, incorporated herein by reference) (1.52 g) in 1 L anhydrous ethanol in a 3-necked round bottom flask fitted with a reflux condenser was degassed with $N_2$ for 15 min and then refluxed for 1 h. Compound B (259 µL) was added via a syringe over 10 min. and the resulting solution was refluxed for 24 h. The dark brown solution was cooled to room temperature and then concentrated to about 80 mL by rotary evaporation. Ethyl ether (about 400 mL) was added and the resulting mixture was degassed for 5 min. After standing at room temperature overnight, the resulting dark brown precipitate of compound C was collected by suction filtration. Yield: about 1 g.

Quaternization of Poly(4-vinylpyridine) with 6-Bromohexanoic Acid

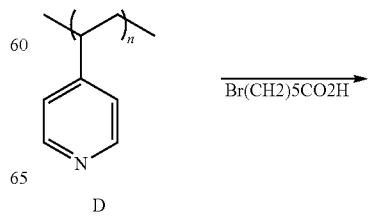

-continued

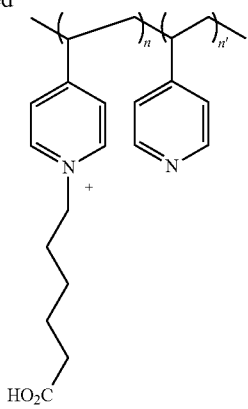

E

To compound D (2 g) dissolved in DMF was added 6-bromohexanoic acid (0.56 g). The resulting solution was stirred at 90° C. for 24 h. The solution was poured into 200 mL EtOAc under rapid stirring. The precipitate was collected by suction filtration, washed with EtOAc (2×20 mL) and then dried under high vacuum at 50 to 60° C. for 2 days. NMR ($d_6$-DMSO) indicated that about 15% of the pyridyl groups in the polymer were quatemized. Yield: 2.1 g.

Synthesis of Polymeric Osmium Complex G

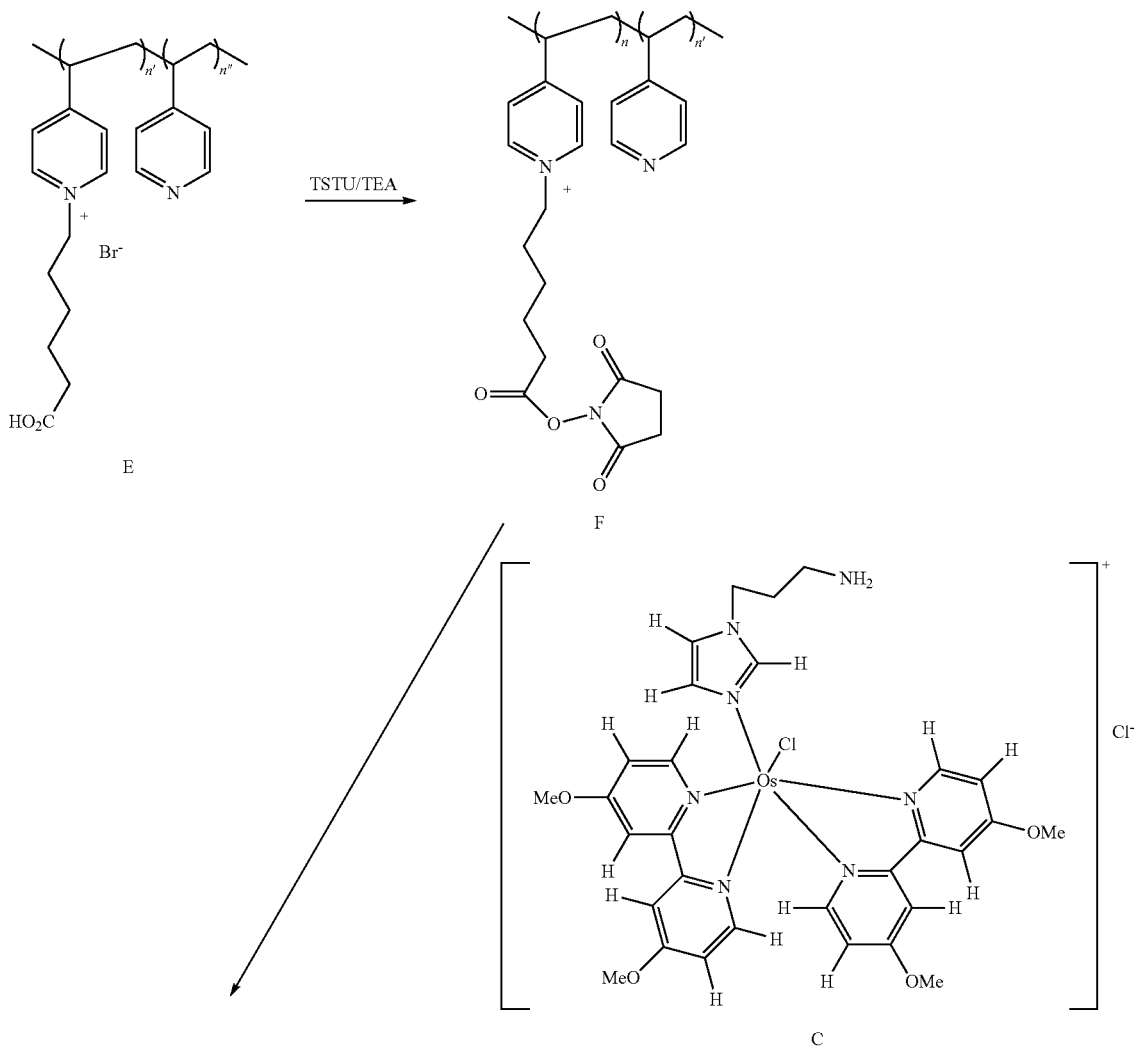

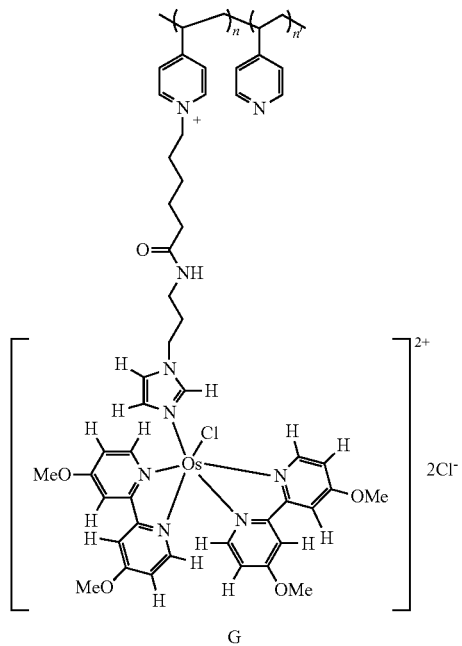

G

To a solution of compound E (71 mg) in 4 mL dry DMF was added O—(N-succinimidyl)-N,N,N',N'-tetramethyluronium tetrafluoroborate (TSTU) (24 mg). After the solution was stirred for 30 min, N,N,N-diisopropylethylamine (14 µL) was added and the resulting solution was stirred for 4 h. Compound C was added at once, followed by addition of another 14 µL N,N,N-diisopropylethylamine. The solution was continued to stir at room temperature for another 24 h. The dark brown solution was poured into 100 mL ether. The precipitate was collected by suction filtration, washed with ether (20 mL) and dried under vacuum at 50° C. for 24 h. The crude product was mixed with 30 mL chloride resin (AG 1×4, Bio-Rad Laboratories, Inc., Hercules, Calif.) in 50 mL $H_2O$ and the resulting mixture was stirred in open air for 24 h. As the stirring continued, the insoluble polymeric Os(II) complex was slowly oxidized by air to the water soluble polymeric Os(III) complex with chloride as counter anions. The mixture was suction filtered and the filtrate was dialyzed by repeated ultrafiltration with $H_2O$ (ultrafiltration membrane from Millipore, Corp., Bedford, Mass.: PM10, NMWL/10,000). The dialyzed polymer concentrate was diluted with $H_2O$ to 10 mL and then freeze-dried to give compound G. Yield: 80 mg.

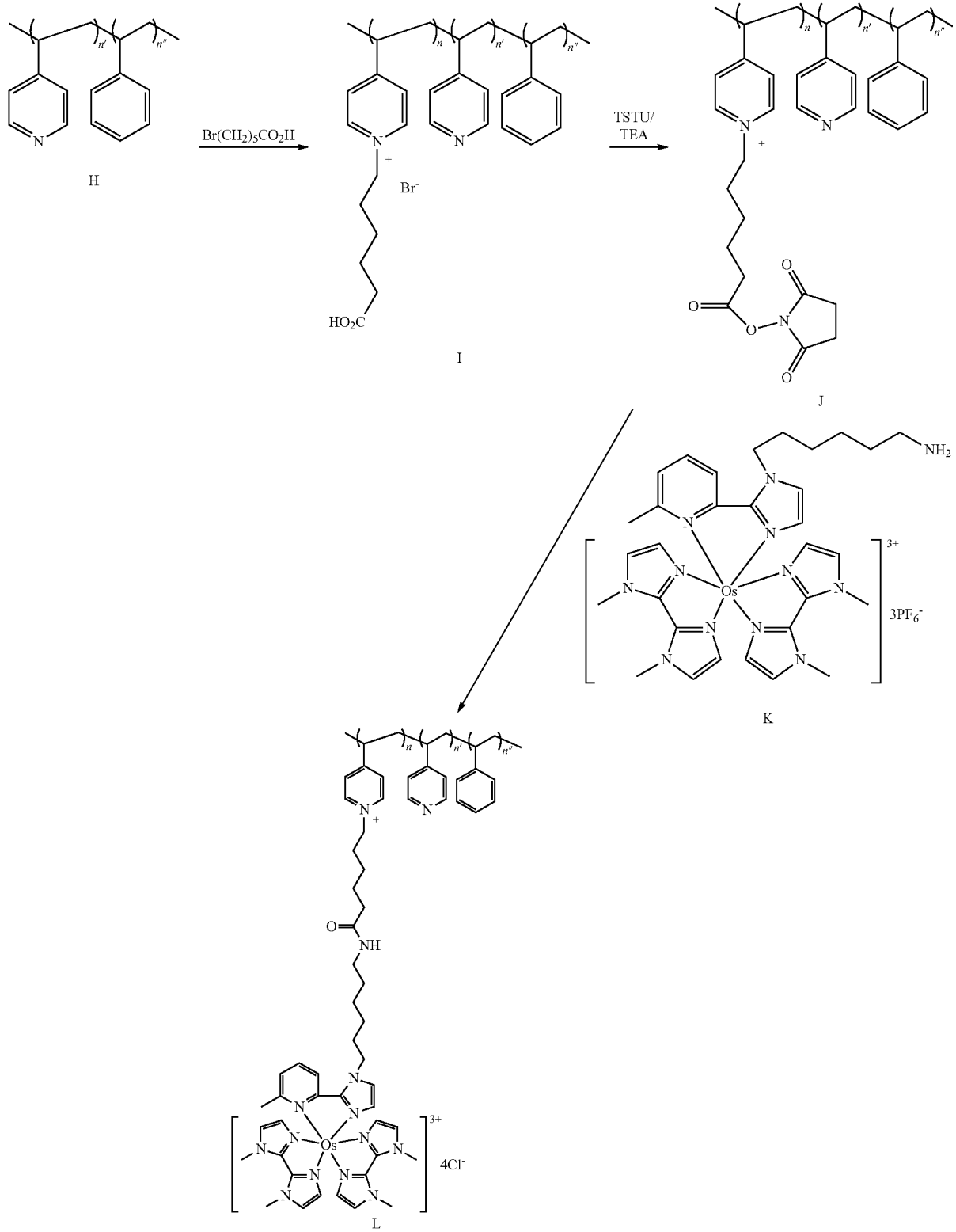

Synthesis of Compound I: Compound H (10% styrene, Aldrich)(2.37 g) was dissolved in DMF (20 mL) by stirring the mixture at 90° C. for 3-4 h. 6-Bromohexanoic acid (0.66 g) was added portionwise over 10 min. and the resulting solution was stirred at 90° C. for 24 h. The solution was poured into 300 mL EtOAc and the precipitate was collected by suction filtration. The gummy product was redissolved in a minimum of methanol and precipitated out with ether (200 mL). The product was dried under high vacuum at 50° C. for 2 days.

Synthesis of 2-(6-Methyl-2-pyridyl)imidazole: A solution of 6-methylpyridine-2-carboxaldehyde (26 g, 0.21 mole) and glyoxal (40%, 30 mL) in 50 mL EtOH in a three-necked 250 mL round bottom flask fitted with a thermometer and an addition funnel was stirred in a NaCl/ice bath. When the solution was cooled to below 5° C., conc. $NH_4OH$ was added dropwise through the addition funnel. The rate of the addition was controlled so that the temperature of the solution was maintained at below 5° C. After the addition, the stirring of the yellow solution was continued in the ice bath for 1 h and then at room temperature overnight. The light yellow crystals were collected by suction filtration and washed with $H_2O$ (20 mL). The crystals were resuspended in $H_2O$ (200 mL) and boiled briefly, followed by suction filtration, to collect the product which was dried under high vacuum. Yield: 35%.

Synthesis of 2-(6-methyl-2-pyridyl)-1-(6-(phthalimido) hexyl)imidazole: To a solution of 2-(6-Methyl-2-pyridyl) imidazole (2.16 g) and sodium t-butoxide (1.57 g) in 50 mL dry DMF was added N-(6-bromohexyl)phthalimide (4.72 g). The resulting solution was stirred at room temperature for 3 h and then at 60° C. for 3.5 h. The solution was poured into $H_2O$ (80 mL) and then extracted three times with EtOAc (3×100 mL). The combined EtOAc extract was dried with anhydrous $Na_2SO_4$, and then evaporated to dryness. The product was purified by a silica gel column using EtOAc as the eluent. Yield: about 4.2 g.

Synthesis of 1-(6-Aminohexyl)-2-(6-methyl-2-pyridyl) imidazole: To a solution of 2-(6-methyl-2-pyridyl)-1-(6-(phthalimido)hexyl)imidazole (4.2 g) in 50 mL EtOH was added 1.5 mL hydrazine hydrate. The resulting solution was stirred at 80° C. overnight. The solution was cooled to room temperature and suction filtered to remove the precipitate. The filtrate was evaporated to give the crude product, which was purified by a silica gel column using 5% conc. $NH_3H_2O/CH_3CN$ as the eluent. Yield: about 2.5 g.

Synthesis of 1,1'-Dimethyl-2,2'-biimidazole: To a stirred solution of 2,2'-biimidazole (Fieselmann, B. F., et al. *Inorg. Chem.* 17, 2078(1978)) (4.6 g, 34.3 mmoles) in 100 mL dry DMF in a 250 ml round bottom flask cooled in an ice/water bath was added in portions NaH (60% in mineral oil, 2.7 g, 68.6 mmoles). After the solution was stirred at 0° C. for one hour under $N_2$, methyl toluenesulfonate (10.3 mL, 68.6 mmoles) was added in small portions using a syringe over 30 min. The stirring of the solution in the ice/water bath was continued for 1 h and then at room temperature for 3 h. The solvent was removed by vacuum distillation. The dark residue was triturated with ether and then suction filtered and dried under vacuum. The product was purified by sublimation. Yield: 80%.

Synthesis of [Os(1,1'-dimethyl-2,2'-biimidazole)$_2$Cl$_2$]Cl: Potassium hexachloroosmate (1 g, 2.08 mmoles), 1,1'-dimethyl-2,2'-biimidazole (0.67 g, 4.16 mmoles) and LiCl (1 g, 23.8 mmoles) were suspended in 40 mL ethylene glycol in a 250 mL three-necked round bottom flask fitted with a reflux condenser. The suspension was degassed with $N_2$ for 15 min and then stirred under $N_2$ at 170° C. in an oil bath for 7-8 h, resulting in a dark brown solution. The solvent was removed by high vacuum distillation at 90-100° C. bath temperature. The gummy solid was triturated with acetone twice (2×50 mL) and then with $H_2O$ once (50 mL). The product was dried at 50° C. under high vacuum for 24 h.

Synthesis of Compound K: A mixture of [Os(1,1'-dimethyl-2,2'-biimidazole)$_2$Cl$_2$]Cl (0.525 g) and 1-(6-aminohexyl)-2-(6-methyl-2-pyridyl)imidazole (0.248 g) is 40 mL ethylene glycol was degassed with $N_2$ for 10 min and then stirred under $N_2$ at 140° for 24 h. Ethylene glycol was removed by high vacuum distillation at 90° C. The residue was dissolved in 150 mL $H_2O$ and the resulting solution was stirred in open air for 24 h to allow full oxidation of Os(II) to Os(III). The solution was poured into a rapidly stirred solution of $NH_4PF_6$ (4.2 g) in 100 mL $H_2O$. The precipitate was collected by suction filtration and washed with $H_2O$ (2×10 mL). The 25 crude product was redissolved in 15 mL $CH_3CN$ and then added to a stirred solution of $NH_4PF_6$, (2.2 g) in 200 mL $H_2O$. The resulting precipitate was collected by suction filtration, washed with $H_2O$ (10 mL) and then dried under high vacuum at 45° C. Yield: about 0.6 g.

Synthesis of Compound L: the polymeric osmium complex was synthesized from polymer I and complex K using the method described above for compound G.

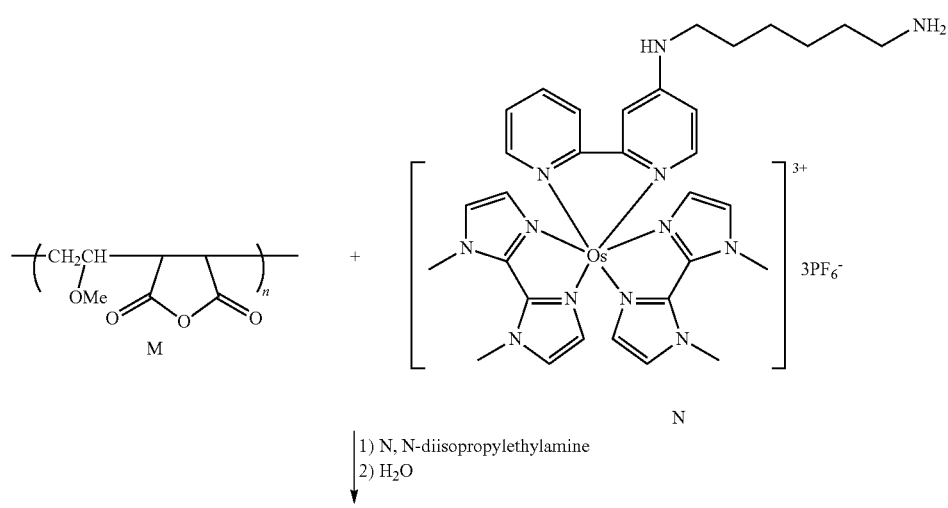

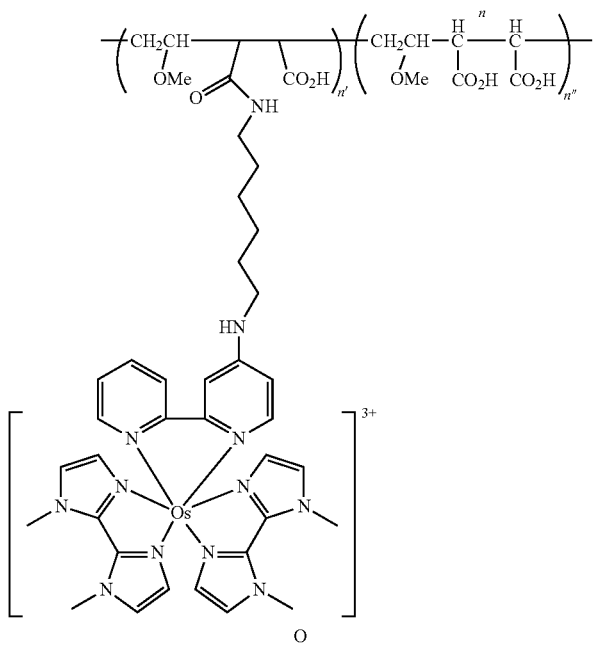

Synthesis of 4-bromo-2,2'-bipyridyl-N-oxide: To 4-nitro-2,2'-bipyridyl-N-oxide (Wenkert, D.; Woodward, R. B. *J. Org. chem.* 48,283(1983)) (5 g) dissolved in 30 mL acetic acid in a 100 ml round bottom flask was added 16 mL acetyl bromide. The yellow mixture was refluxed for 1.5 h and then rotovaporated to dryness. The resulting light yellow solid was sufficiently pure enough for the next step without further purification. Yield: 95%

Synthesis of 4-bromo-2,2'-bipyridyl: To a stirred suspension of 4-bromo-2,2'-bipyridyl-N-oxide in 60 mL $CHCl_3$, was added 12 mL $PCl_3$, at room temperature. The mixture was refluxed for 2 h under $N_2$ and then cooled to room temperature. The reaction mixture was poured into 100 mL ice/water. The aqueous layer was separated and saved. The $CHCl_3$, layer was extracted three times with $H_2O$ (3×60 mL) and then discarded. The combined aqueous solution was neutralized with $NaHCO_3$ powder to about pH 7-8. The resulting white precipitate was collected by suction filtration, washed with $H_2O$ (30 mL) and then dried under vacuum at 50° C. for 24 h. Yield: 85%.

Synthesis of a 4-((6-aminohexyl)amino)-2,2'-bipyridine: A mixture of 4-bromo-2,2'-bipyridyl (2.5 g) and 1,6-diaminohexane (15 g) in a 250 mL round bottom flask was heated under $N_2$ at 140° C. in an oil bath for 4-5 h. Excess 1,6-diaminohexane was removed by high vacuum distillation at 90-120° C. The product 20 was purified by a silica gel column, eluting with 5% $NH_4OH$ in isopropyl alcohol. Yield: 70%.

Synthesis of Compound N: Compound N was made from 4-((6-aminohexyl)amino)-2,2'-bipyridine and [Os(1,1'-dimethyl-2,2'-biimidazole)$_2$Cl$_2$]Cl using the method described for compound K.

Synthesis of Compound O: To a solution of compound M (37 mg, International Specialty Products, Wayne, N.J., USA) in 2 mL $CH_3CN$ and 0.5 mL THF was added compound N (51 mg), followed by the addition of two drops of N,N,N-diisopropylethylamine. The resulting solution was stirred at room temperature for 24 h. $H_2O$ (5 mL) was added and the solution was stirred for another 24 h. The solution was diluted with more $H_2O$ (50 mL) and dialyzed by repeated ultrafiltration as described above for the purification of compound G. The dialyzed solution was freeze-dried to give compound O.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

That which is claimed is:

1. An analyte sensor comprising:
   a substrate comprising a non-conductive base material, wherein the substrate comprises a first surface and a second surface that is opposite the first surface;
   a counter electrode disposed on the first surface of the substrate;
   a working electrode comprising a conductive layer disposed on the second surface of the substrate; and
   a reagent positioned on the working electrode, the reagent comprising:
   an analyte responsive enzyme; and
   a mediator comprising a plurality of polymeric transition metal complexes, each transition metal complex having the formula:

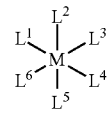

wherein M is osmium,
$L^1$ is a ligand comprising a heterocycle and is coordinatively bound to M via a heteroatom of the heterocycle, $L^2$, $L^3$, $L^4$, $L^5$, and $L^6$ are ligands comprising a nitrogen-containing heterocycle, wherein each of $L^1$, $L^2$, $L^3$, $L^4$, $L^5$, and $L^6$ ligands is independently a monodentate ligand or is combined with at least one other ligand to form a multidentate ligand, and wherein at least one of $L^1$, $L^2$, $L^3$, $L^4$, $L^5$, and $L^6$ is covalently coupled to the at least one spacer;

a polymer backbone; and at least one spacer attached to the polymer backbone, the at least one spacer comprising at least one non-cyclic functional group selected from the group consisting of —(CR$^r$R$^s$)—, —O—, —S—, —C(O)O—, —S(O)$_2$NR$^k$—, —OC(O)NR$^m$—, —OC(S)NR$^n$—, —C(O)NR$^t$—, —NR$^u$—, —CR$^v$=N—O—, —CR$^w$=NNR$^x$—, and —(SiR$^y$R$^z$)—, and wherein R$^r$ and R$^s$ are independently hydrogen, chlorine, fluorine, or substituted or unsubstituted alkyl, alkoxy, alkenyl, or alkynyl, and R$^k$, R$^m$, R$^n$, R$^t$, R$^u$, R$^v$, R$^w$, R$^x$, R$^y$, and R$^z$ are independently hydrogen or substituted or unsubstituted alkyl.

2. The analyte sensor of claim 1, wherein the analyte-responsive enzyme is an enzyme selected from the group consisting of glucose oxidase and glucose dehydrogenase.

3. The analyte sensor of claim 1, wherein the polymer backbone comprises a nitrogen containing heterocyclic ring.

4. The analyte sensor of claim 1, wherein the nitrogen-containing heterocycle comprises a substituted or unsubstituted pyridine, imidazole, 2,2'-bipyridine, 2-(2-pyridyl)imidazole, or 2,2'-biimidazole.

5. The analyte sensor of claim 1, wherein at least two of $L^1$, $L^2$, $L^3$, $L^4$, $L^5$, and $L^6$ are combined to form at least one multidentate ligand.

6. The analyte sensor of claim 1, wherein at least four of $L^1$, $L^2$, $L^3$, $L^4$, $L^5$, and $L^6$ are combined to form at least two multidentate ligands.

7. The analyte sensor of claim 1, wherein at least four of $L^1$, $L^2$, $L^3$, $L^4$, $L^5$, and $L^6$ are combined to form at least two multidentate ligands selected from the group consisting of substituted and unsubstituted 2,2'-bipyridines, 2-(2-pyridyl)imidazoles, and 2,2'-biimidazoles.

8. The analyte sensor of claim 7, wherein the mediator comprises at least one substituted or unsubstituted 2,2'-biimidazole or 2-(2-pyridyl)imidazole.

9. The analyte sensor of claim 1, wherein the mediator has the formula:

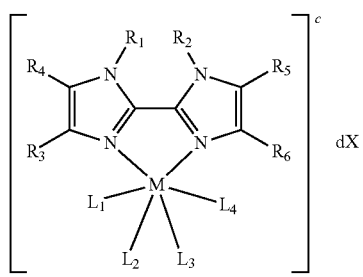

wherein M is osmium;

$R_1$ and $R_2$ are independently substituted or unsubstituted alkyl;

$R_3$, $R_4$, $R_5$, and $R_6$ are independently —H, —F, —Cl, —Br, or substituted or unsubstituted C1 to C12 alkyl;

c is an integer selected from −1 to −5 or +1 to +5 indicating a positive or negative charge;

X represents at least one counter ion; and d is an integer from 1 to 5 representing the number of counter ions, X.

10. The analyte sensor of claim 1, wherein the mediator has the formula:

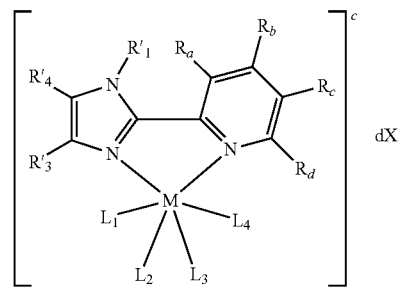

wherein M is osmium;

$R'_1$ are substituted or unsubstituted alkyl;

$R'_3$ and $R'_4$ and independently —H, —F, —Cl, —Br, or substituted or unsubstituted C1 to C12 alkyl;

$R_a$, $R_b$, $R_c$, and $R_d$ are independently —H, —F, —Cl, —Br, —CN, —CO$_2$H, —SO$_3$H, —NO$_2$, —NH$_2$, —NHNH$_2$, —SH, or substituted or unsubstituted C1 to C12 alkylamino, C2 to C24 dialkylamino, C1 to C12 alkoxy, or C1 to C12 alkyl;

c is an integer selected from −1 to −5 or +1 to +5 indicating a positive or negative charge;

X represents at least one counter ion; and d is an integer from 1 to 5 representing the number of counter ions, X.

11. The analyte sensor of claim 1, wherein the mediator has the formula:

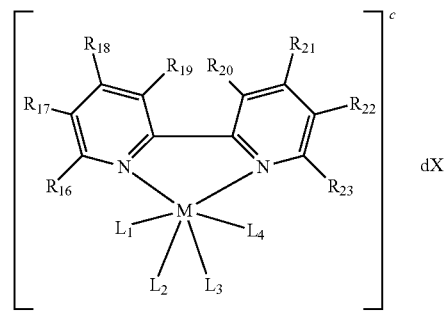

wherein M is osmium;

$R_{18}$ and $R_{21}$ are independently —H, —F, —Cl, —Br, —CN, —CO$_2$H, —SO$_3$H, —NO$_2$, —NH$_2$, —NHNH$_2$, —SH, or substituted or unsubstituted C1 to C12 alkylamino, C2 to C24 dialkylamino, C1 to C12 alkoxy, or C1 to C12 alkyl;

$R_{16}$, $R_{17}$, $R_{19}$, $R_{20}$, $R_{22}$ and $R_{23}$ —H or substituted or unsubstituted C1 to C12 alkyl;

c is an integer selected from −1 to −5 or +1 to +5 indicating a positive or negative charge;

X represents at least one counter ion; and d is an integer from 1 to 5 representing the number of counter ions, X.

12. The analyte sensor of claim 1, wherein the analyte-responsive enzyme further comprises an enzyme cofactor.

13. The analyte sensor unit of claim 12, wherein the enzyme cofactor is flavin adenine dinucleotide.

14. The analyte sensor of claim 1, wherein the polymer is crosslinked.

15. The analyte sensor of claim 1, wherein the spacer comprises —C(O)O— or —S(O)$_2$NR$^k$—, wherein R$^k$, is hydrogen or substituted or unsubstituted alkyl.

16. The analyte sensor of claim 1, wherein the spacer comprises —C(O)NR$^t$—.

17. The analyte sensor of claim 1, wherein the spacer comprises —(CR$^r$R$^s$)—, wherein R$^r$ and R$^s$ are independently hydrogen, chlorine, fluorine, or substituted or unsubstituted alkyl, alkoxy, alkenyl, or alkynyl.

18. The analyte sensor of claim 1, wherein the spacer comprises —O— or —S—.

19. The analyte sensor of claim 1, wherein the spacer comprises —CR$^v$=N—O— or —CR$^w$=NNR$^x$—, wherein R$^v$, is hydrogen or substituted or unsubstituted alkyl and wherein R$^w$ and R$^x$ are independently hydrogen or substituted or unsubstituted alkyl.

20. The analyte sensor of claim 1, wherein the spacer comprises —(SiR$^y$R$^z$)—, wherein R$^y$ and R$^z$ are independently hydrogen or substituted or unsubstituted alkyl.

* * * * *